US010131920B2

(12) United States Patent
Dieci et al.

(10) Patent No.: US 10,131,920 B2
(45) Date of Patent: Nov. 20, 2018

(54) NUCLEIC ACID MOLECULES

(71) Applicant: MEDIMMUNE LIMITED, Cabmbridge (GB)

(72) Inventors: Giorgio Dieci, Parma (IT); Marcello Marelli, Seattle, WA (US); Kenneth H. Grabstein, Mercer Island, WA (US)

(73) Assignee: MEDIMMUNE LIMITED, Cambridge (GB)

( * ) Notice: Subject to any disclaimer, the term of this patent is extended or adjusted under 35 U.S.C. 154(b) by 0 days.

(21) Appl. No.: 14/775,684

(22) PCT Filed: Mar. 14, 2014

(86) PCT No.: PCT/EP2014/055210
§ 371 (c)(1),
(2) Date: Sep. 12, 2015

(87) PCT Pub. No.: WO2014/140347
PCT Pub. Date: Sep. 18, 2014

(65) Prior Publication Data
US 2016/0024522 A1 Jan. 28, 2016

Related U.S. Application Data

(60) Provisional application No. 61/843,959, filed on Jul. 9, 2013, provisional application No. 61/801,029, filed on Mar. 15, 2013.

(51) Int. Cl.
C12N 15/85 (2006.01)
C12N 15/67 (2006.01)
C12P 21/00 (2006.01)

(52) U.S. Cl.
CPC ............. *C12N 15/85* (2013.01); *C12N 15/67* (2013.01); *C12P 21/00* (2013.01); *C12N 2800/107* (2013.01)

(58) Field of Classification Search
None
See application file for complete search history.

(56) References Cited

U.S. PATENT DOCUMENTS

| 3,711,458 | A | 1/1973 | Olofson |
| 4,512,979 | A | 4/1985 | Patchett |
| 5,216,023 | A | 6/1993 | Nagy |
| 8,168,407 | B2 | 5/2012 | Yokoyama |
| 9,670,521 | B2 | 6/2017 | Grabstein et al. |
| 9,732,367 | B2 | 8/2017 | Grabstein et al. |
| 2009/0155844 | A1 | 6/2009 | Yokoyama et al. |
| 2010/0304431 | A1 | 12/2010 | Yokoyama et al. |
| 2017/0306380 | A1 | 10/2017 | Grabstein et al. |
| 2017/0306381 | A1 | 10/2017 | Grabstein et al. |

FOREIGN PATENT DOCUMENTS

| EP | 1911840 A1 | 4/2008 |
| GB | 2470770 A | 12/2010 |
| JP | 2012-506869 A | 3/2012 |
| WO | 2004/041752 A2 | 5/2004 |
| WO | 2010/048582 A1 | 4/2010 |
| WO | 2011/044255 A1 | 4/2011 |
| WO | 2011/087810 A1 | 7/2011 |
| WO | 2012/032181 A9 | 3/2012 |
| WO | 2012/038706 A1 | 3/2012 |
| WO | WO 2012038706 A1 * | 3/2012 ............ C12N 15/09 |
| WO | 2014/036492 A1 | 3/2014 |

OTHER PUBLICATIONS

Mukai et al. (2008) Adding L-lysine derivatives to the genetic code of mammalian cells with engineered pyrrolysyl-tRNA synthetases. Biochemical and Biophysical Research Communications, 371(4):818-822.*
Kriegs et al. (2007) Evolutionary history of 7SL RNA-derived SINEs in Supraprimates. TRENDS in Genetics, 23(4):158-161.*
Mukai et al. (2008) Adding L-lysine derivatives to the genetic code of mammalian cells with engineered pyrrolysyl-tRNA synthetases. Biochemical and Biophysical Research Communications, 371:818-822.*
Hancock et al. (2010) Expanding the Genetic Code of Yeast for Incorporation of Diverse Unnatural Amino Acids via a Pyrrolysyl-tRNA Synthetase/tRNA Pair. Journal of the American Chemical Society, 132:14819-14824.*
Korkhin et al. (2009) Evolution of Complex RNA Polymerases: The Complete Archaeal RNA Polymerase Structure. PLoS Biology, 7(5):e1000102, pp. 1-10.*
Axup et al, "Synthesis of site-specific antibody-drug conjugates using unnatural amino acids", P.N.A.S. 109(40), (2012) 16101-16106.
Coward et al, "Analogs of S-adenosylhomocysteine as potential inhibitors of biological transmethylation. Synthesis and biological activity of homocysteine derivatives bridged to adenine", J. Med. Chem., 15(4), 381-384 (1972).
Dose et al, "Single nucleotide specific detection of DNA by native chemical ligation of fluorescence labelled PNA-probes", Bioorg. Med. Chem., 16, (2008) 65-77.
Erickson et al, "Use of chlorinated benzyloxycarbonyl protecting groups to eliminate N. epsilon-branching at lysine during solid-phase peptide synthesis", J.A.C.S., 95(11), 3757-3763 (1973).
Hancock et al: "Expanding the Genetic code of Yeast for Incorporation of diverse unnatural amino acids via a pyrrolysyl-tRNA synthetase/tRNA pair"; J.A.C.S., 132(42), 14819-14824 (2010).
Jermyn "Carbobenzoxy derivatives of S-aminoalkyl-L-cysteines", Australian Journal of Chemistry, 19(10), 1999-2000 (1966).
Jie Li et al: "Ligand-free palladium-mediated site-specific protein labelling inside gram-negative bacterial pathogens", J.A.C.S., 135(19), 7330-7338, (2013).

(Continued)

*Primary Examiner* — Neil P Hammell
(74) *Attorney, Agent, or Firm* — Medler Ferro Woodhouse & Mills, PLLC

(57) ABSTRACT

There is provided inter alia a DNA construct which comprises a tRNApyl coding sequence and a RNA polymerase III promoter sequence which is capable of acting to express functional tRNApyl sufficiently to support nonsense suppression in a eukaryotic expression system.

17 Claims, 8 Drawing Sheets

Specification includes a Sequence Listing.

(56) References Cited

OTHER PUBLICATIONS

Kimbonguila et al, "Allylic protection of thiols and cysteine: I: The allyloxycarbonylaminomethyl group", Tetrahedron, 55(22), 6931-6944 (1999).

Ledger et al, "The use of sequestering agents in the preparation of [epsilon]-acyl-L-lysine and [delta]-acyl-L-ornithine derivatives", Australian Journal of Chemistry, 18(6), 933-935, (1965).

Lindley "The preparation of compounds related to S-2-aminoethyl-L-cysteine" Australian Journal of Chemistry 12(2), 296-298, (1959).

Matsui, "Studies on acylase activity and microorganisms. XXIV. Properties of [delta]-ornithine acylase: 5-N-acylornithine amidohydrolase", Chem. Pharm. Bull., 15(10), 1586-1596 (1967).

Mukai et al: "Adding L-lysine derivatives to the genetic code of mammalian cells with engineered pyrrolysyl-tRNA synthetases"; Biochem. Biophys. Res., 371(4), 818-822 (2008).

Nishino et al, "Tandem enzymatic relsolution yielding L-alpha-aminoalkanedioic acid omega-esters", Chem. Pharm. Bull., 44(1), 212-214 (1996).

Noda et al, "Modified benzyloxycarbonyl groups for protection of [epsilon]-amino group of lysine", Bull. Chem. Soc. Japan, 43(6), 1883-1885 (1970.

Plass et al, "Genetically encoded copper-free click chemistry", Angewandte Chemie, Int Edition, 50(17), 3878-3881 (2011).

Popovitz-Biro et al, "A new series of amphiphilic molecules forming stable Z-type (polar) Langmuir-Blodgett films", 112(7), 2498-2506 (1990).

Spanton et al, "Chemical defence and self-defence: Biochemical transformations of contact insecticides produced by soldier termites", Tetrahedron, 38(13), 1921-1930 (1982).

Theodoropoulos, "Synthesis of [epsilon]-peptides of lysine", J. Org. Chem. 23(1), 140, (1958).

Vrabel et al, "Optimization of the posttranslational click modification of proteins", Collect. Czech. Chem. Commun. 76(9), (2011) 1089-1101.

Xin Li et al, "N6-(2-(R)-propargylglycyl)lysine as a clickable pyrrolysine mimic", Chemistry—An Asian Journal, 5(8), 1765-1769 (2010).

Yasobu et al, "Design, Synthesis and Antitumor Activity of 4-Halocolchicines and their Pro-drugs Activated by Cathepsin B", ACS Med. Chem. Lett., 2, (2011) 348-352.

Zhang et al, "Mechanism of inactivation of neuronal nitric oxide synthase by N[omega]-allyl-L-arginine", J.A.C.S., 119(45), 10888-10902 (1997).

International search report of PCT/IB2014/002505 (8 pages), dated Jul. 4, 2015.

International search report of PCT/EP2013/069887 (5 pages), dated Jul. 4, 2015.

International search report of PCT/EP2013/069888 (4 pages), dated Mar. 1, 2014.

Sun et al., "Vitamin K epoxide reductase significantly improves carboxylation in a cell line overexpressing factor X", Blood, 106(12):3811-3813 (2005).

International Search Report dated Nov. 14, 2013, in PCT/EP2013/069887 (5 pages).

International Search Report dated Jan. 3, 2014, in PCT/EP2013/069888 (4 pages).

International Search Report dated Jul. 4, 2015, in PCT/IB2014/002505 (8 pages).

Office Action dated Aug. 7, 2018 in corresponding Japanese Patent Application No. 2015-562250.

\* cited by examiner

FIG. 1E

Vault ATGGGTCGCTGAGTCATGCTGAAGCACTCTCTTTTGACTCACTCTTGTGACGTAGGTCTTTCTCACCAGTCAATAAAATATAATCCGAAAAGCAA[?]TCCCACCA Sp1　　　　　　　　ATF　　　　　　　TATA　　　　　TSS EBER GCACGCTAACCCCGCCTACACCGGTGACGTAGCTGTTACCAGCATGTATAGAGTTACGGTTCGCTACATCAAACACCA

ATF/CRE　　　　　ETAB　　　　TSS

7SL CCAGTAGATATCCCAGTTGATGACGTCACCATACCACAGCTTCTAGTGCTATTCTGCGCCGGTATCCGACCACCA

FIG. 2

```
 1  GGAAACCTGA TCATGTAGAT CGAATGGACT CTAAATCCGT TCAGCCCGGT TAGATTCCCG GGGTTTCCG  69
              A-BOX                                          B-BOX
             10         20         30         40         50         60
```

FIG. 3

```
                      1              10             20             30             40             50             69
Mb pyltRNA      (1) GGGAACCTGATGATCATGTAGATCGAATGGACTCTAAATCCGTTCAGCCGGGTTGATTCCCGGGGTTTCCG
Mm pyl tRNA     (1) GGGAACCTGATCATCATGTAGATCGAATGGACTCTAAATCCGTTCAGCCGGGTTGATTCCCGGGGTTTCCG
Mb pyltRNA(A+B box) (1) GGGAACCTGGTCAGGTAGAACGAATGGACTCTAAATCCGTTCAGCCGGGTTAGATTCCCGGGGTTTCCG
Mm pyl tRNA(A+B box) (1) GGGAACCTGGTCAGGTAGAACGAATGGACTCTAAATCCGTTCAGCCGGGTTAGATTCCCGGGGTTTCCG
```

NUCLEIC ACID MOLECULES

CROSS-REFERENCE TO RELATED PATENT APPLICATIONS

The present invention is filed under 35 U.S.C. § 371 as the U.S. national phase of International Application No. PCT/EP2014/055210, filed Mar. 14, 2014, which designated the United States and claims the benefit of U.S. Provisional Application No. 61/801,029, filed Mar. 15, 2013, and to U.S. Provisional Application No. 61/843,959, filed Jul. 9, 2013, each of which is hereby incorporated by reference in its entirety including all tables, figures, and claims.

SEQUENCE LISTING

The instant application contains a Sequence Listing which has been submitted in ASCII format via EFS-Web and is hereby incorporated by reference in its entirety. Said ASCII copy, created on Nov. 28, 2016, is named 304_0042USWO_SeqListing_2.txt and is 30 kilobytes in size.

FIELD OF THE INVENTION

This invention relates inter alia to novel nucleic acid molecules, vectors containing them, eukaryotic host cells and host cell lines transformed with said vectors and their use in protein production, especially production of proteins containing non-natural amino acids.

INTRODUCTION

It has been observed that one orthogonal RS/tRNA pair, naturally evolved in a subset of archaebacteria, (methanogenic archaea bacteria that catabolize methylamines) has specificity for the amino acid pyrrolysine. Pyrrolysine uses a 21st aminoacyl-tRNA synthetase, naturally evolved to be orthogonal to all other amino acids and tRNAs.

Pyrrolysine is a natural amino acid, the only one that is authentically specified by an amber codon. Blight et al., 2004 showed that PylRS and tRNApyl can incorporate Pyrrolysine at amber codons in *E. coli*. They also showed that the wt PyLRS is naturally promiscuous and can incorporate analogs of lysine.

Yokoyama et al (EP1911840) demonstrated that the PylRS/tRNA system is orthogonal in eukaryotic cells and showed the incorporation of several nnAAs into a target proteins encoded by amber codons in bacterial cells. These authors also identified key amino acid residues in pylRS that form the amino acid binding pocket and function in selecting pyrrolysine over other canonical amino acids. Mutations at this site generated mutants able to recognize and aminoacylate the tRNApyl with AzZ-lys (Yanagisawa 2008).

This orthogonality extends to bacteria and eukaryotic cells.

PylRS is a naturally promiscuous synthetase that has naturally evolved to exclude lysine, but will incorporate lysine analogs without mutation, including azides, alkynes and alkenes, (Yanagisawa et al, 2008; Neumann et al. 2008; Mukai et al., 2008; Nguyen et al., 2009). The basis of this specificity is dependent on hydrophobic interactions between amino acid residues of the pylRS binding pocket with the pyrrole ring of pyrrolysine that stabilizes and correctly positions the amino acid in the active site of the synthetase (Kavran et al., 2007). This RS/tRNA pair has been introduced via transient transfection into bacterial, yeast and mammalian cells and shown to be effective for incorporation of a number of non-natural amino acids into target proteins.

For instance, EP 1911840 demonstrates incorporation of N-ε-boc-Lysine into a target protein in *E. coli* cells.

The expression of tRNA in eukaryotic cells is carried out by RNA polymerase III ("PolIII"), requiring a type 2 intragenic promoter that contains a bipartite structure, in which two short conserved sequence elements known as an A-box and a B-box are separated by a variable sequence. In contrast to mammalian tRNA genes, prokaryotic tRNA genes are regulated by extragenic promoter elements. As a consequence, many prokaryotic tRNAs do not contain A-box and B-box elements that function as promoters in mammalian cells. This is the case for the *Methanosarcina* derived tRNApyl.

Introduction of a tRNApyl coding sequence into mammalian cells, along with PylRS, did not result in amber suppression of a reporter construct, presumably due to the lack of conserved A- and B-box elements (Mukai, et al., 2008).

Hancock et al (Hancock et al, 2010. JACS) attempted to reconstruct a functional A-Box and B-Box within the tRNApyl gene from *Methanosarcina barkeri*, and failed to demonstrate functional amber suppression of the mutated tRNA genes in yeast, suggesting that any modifications to introduce an A- and B-box elements into the tRNA sequence alters the tRNA architecture, hindering its overall function. Sequence analysis of the Mm tRNApyl shows that the B-box has significant homology to a consensus B-box, but the A-box shows significant divergence.

Attempts to find optimal conditions to express suppressor tRNAs in mammalian cells date back to 1982 (Hudziak et al, 1982, Laski et al, 1982) in the context of generating nonsense suppressor tRNAs for gene therapy of genetic diseases where a stop codon caused early termination of transcription of a key protein.

The amount of DNA introduced into cells, the number of copies of the tRNA gene as well as the promoter elements driving its expression have been identified as key elements to reach optimal tRNA level, e.g. to allow efficient activity without causing toxicity to the cell.

The expression of tRNA by processing of a bicistronic construct has been shown to exist in eukaryotic cells. A genomically encoded gene pair for tRNAarg-tRNAasp has been described in yeast cells (Schmidt et al. 1980). This gene is expressed as a single precursor RNA that is posttranscriptionally modified to generate two mature tRNAs in vivo and in oocyte cell extracts (Schmidt et al. 1980). In this case the tRNA genes are separated by a short spacer region consisting of CTTTGTTTCT (SEQ ID No. 68). This gene arrangement has also been used to express tRNAs that are not normally expressed in yeast (Francis et al 1990). Here, the human tRNAmet gene, which contains consensus A and B-box elements, but is not transcribed in yeast, was successfully expressed in yeast cells when placed downstream of a tRNAarg element. The authors show that the distance of the two RNA genes affects transcriptional efficiency. Expression of the exogenous tRNA was achieved when the two tRNAs were separated by a short 10 bp thymidine rich spacer found between the yeast Arg-Asp tRNA pair. Expression of the tRNAmet gene was also observed when this spacer length was increased (up to 92 bp) of intervening sequence but with lower efficacy (Francis et al., 1990). In another example, Straby (1988) utilized the bicistronic yeast Arg-Asp tRNA gene pair to express the normally transcriptionally silent suppressor tRNAsup (tyr). In one construct, the tRNAsup replaced the tRNAasp gene and retained the short 10 bp thymidine rich spacer found between the yeast Arg-Asp tRNA pair and showed efficient tRNAsup expression.

tRNAs have also been expressed under external promoters such as the U6 promoter (Koukuntla et al., 2013 Mukai et al. 2008), T7 RNA polymerase promoter (Mukai et al. 2008), SNR52 (Wang and Wang, 2012) and as a component of a bicistronic construct regulated by an upstream tRNA gene (Hancock et al., 2010; Francis et al., 1990; Straby 1988; Schmidt et al., 1980; Mukai et al. 2008); as multimers such as the tRNAser (Buvoli et al., 2000)

A variety of extragenic promoters were examined for the expression of tRNApyl by Mukai et al. (see also U.S. Pat. No. 8,168,407) as well as by Hancock et al. These included a human tRNA, e.g. tRNAval or tRNAarg as bicistronic constructs. Whilst the bicistronic system was functional in yeast cells (see Hancock et al), Mukai et al. (2008) reported that in eukaryotic cells placing tRNApyl gene downstream to a eukaryotic tRNA (tRNAval) gene resulted in suboptimal expression of tRNApyl, which was not ideal as levels of expression were too low for optimal amber suppression in mammalian cells.

Further, Mukai et al. (2008) and Hancock et al. (2010) tested the PolIII dependent CMV promoter for the expression of tRNApyl as well as the phage T7 polymerase promoter, and the PolIII/type 3 promoter of the gene for the small nuclear RNA U6. In particular, the authors showed that the U6 promoter linked to the 5' end of the coding sequence for the tRNApyl, was particularly efficient in causing amber suppression when introduced into eukaryotic cells along with the PylRS, a nnAA and a target including an amber codon.

The promoters for the snRNA gene U6 and H1 have been extensively used for the expression of RNA species in mammalian cells. These promoters are particularly useful as expression tools given their function as extragenic promoters. Furthermore, they enable very high expression of genes that are placed downstream of these elements.

However, U6 and H1 promoters have recently been shown to have deleterious effects in cells transfected with these constructs leading to cytotoxicity that is believed to occur due to the high transcriptional demands of this promoter (Ehlert, et al., 2010) (Giering, et al., 2008) (Stegmeier, et al., 2005). Furthermore, the U6 promoter in particular has been shown to affect the localization of the RNA product, leading to its prevalent accumulation in the nucleus, thus posing a problem for its utilization by cytoplasmic machineries (Paul et al., 2003).

While the use of extragenic promoters described above led to the expression of high levels of tRNApyl, it is likely that a majority of the tRNA expressed is mislocalised in the nuclear compartment and unavailable for aminoacylation in the cytosol. Although efficient amber suppression was observed, it is possible that this was due to the relatively small proportion of tRNA that escaped the nucleus.

Hence, it is desirable to engineer an alternative tRNA promoter to allow for better localization of the tRNA and its availability to the translation machinery.

It is also desirable to engineer a tRNA promoter that obviates the cellular toxic effects that have been reported for external promoters such as U6 and H1 promoter elements which may contribute to low levels of protein expression and loss in cell viability in cell lines stably expressing said tRNA constructs.

The RNA polymerase III (sometimes referred to herein as "pol III") transcription machinery is devoted to the production of non-protein coding RNAs (ncRNA) of small size in eukaryotes (reviewed by Dieci et al. 2013).

Pol III-transcribed genes are bound and activated by transcription factors that are selectively recognized by this polymerase. These factors act in a few different combinations, as specified by correspondingly different promoter architectures. These have been classified into three general classes: Type 1 promoters (such as that used by 5S rRNA) contain intragenic elements (promoters are found within the coding sequence of the gene) and consist of an internal control region that is subdivided into an A-box, a C-box and an intermediate element (IE). These elements are necessary for transcription, as they are bound by the basal transcription factors TFIIIC and TFIIIA. Type 2 promoters are used by tRNA genes and contain intragenic promoters that consist of conserved elements known as A-box and B-box. These are the binding sites for the transcription factor TFIIIC, which in turn recruits the initiation factor TFIIIB on an upstream region extending up to position −40 with respect to the transcription start site. Type 3 promoters are extragenic, upstream located promoters and consist of distal and proximal sequence elements and a TATA-box. The promoters for the U6 snRNA and RNase P (H1) RNA are members of this promoter class. These promoters are uniquely recognized by the transcription factor SNAPc (PBP or PTF), which in turn recruits a specific variant of TFIIIB. Interestingly PolIII/Type3 promoters have been adapted for the expression of inhibitory RNA and the expression of tRNA lacking A- and B-box elements in eukaryotic cells, for instance U6 promoters in mammalian cells (Mukai, et al., 2008) and the SNR52 promoter used in yeast (Wang and Wang, 2012).

The expression of several ncRNA genes is regulated by promoter elements placed upstream of the transcribed region, similarly to Type 3 promoters, in combination with intragenic promoters, e.g. A-Box and B-Box used by tRNA genes. These can be considered hybrid promoters—called "Type 4" promoters due to the presence of both extragenic and intragenic control elements. Genes regulated by these promoters include the 7SL (SRP) RNA gene, Vault RNA gene, and the Epstein Barr virus coded small RNA (EBER).

7SL RNA is the RNA component of the signal recognition particle (SRP) that mediates co-translational insertion of secretory proteins into the lumen of the endoplasmic reticulum. Its promoter elements were characterized inter alia in Englert et al., 2004.

Vault RNAs are small RNAs contained in large cytoplasmic ribonucleoprotein particles involved in macromolecular assembly and transport. Its promoter elements were characterized inter alia in Mossink et al., 2002.

EBER gene is a small RNA of unknown function. EBER is encoded by the Epstein-Barr virus genome that is efficiently expressed in mammalian cells and its regulatory promoter elements well characterized (Howe and Shu, Cell 1989). EBER has two known variants—EBER1 and EBER2, EBER2 being expressed at higher levels.

SUMMARY OF THE INVENTION

The inventors have engineered novel DNA constructs for the expression of the tRNApyl genes in eukaryotic cells, especially mammalian cells, under new and improved promoter systems.

The tRNApyl gene sequence possesses two internal regions that resemble an eukaryotic A box and B box, with the B box-like region more closely resembling a functional B box.

Although previous attempts at reconstituting a consensus A-Box and B-box were unsuccessful as reported in Hancock et al (2010) and Mukai et al. (U.S. Pat. No. 8,168,407), the inventors have now surprisingly found that the tRNApyl sequence can be altered to enable a functioning intragenic promoter and obtain a tRNApyl able to mediate efficient amber suppression in combination with WT pylRS.

Such new tRNApyl gene can be used to generate highly active and stable cell lines for the incorporation of nnAAs into cells.

The inventors have also found that the new modified tRNApyl gene containing a functional intragenic promoter element can be further improved by placing them downstream of the 5' regulatory elements of genes expressed under type 4 promoters, thereby reconstituting a functional type 4 promoter element containing both extragenic and intragenic elements.

The inventors have also surprisingly found that the WT tRNApyl gene can be expressed under transcriptional control of a tRNAglu gene and/or a tRNAasp gene, when said tRNAglu gene and/or tRNAasp gene is placed upstream of the tRNApyl gene and altered to lack the transcription termination sequence in order to effectively form a bicistronic message.

DNA constructs bearing tandem repeats of novel tRNApyl genes of the invention have shown to lead to increased amber suppression.

BRIEF DESCRIPTION OF THE FIGURES

FIG. 1E shows promoter sequences containing functional elements that recruit transcription factors that regulate transcription by PolIII RNA polymerase.

FIG. 2. Putative A and B-box regions of the wild type tRNApyl from *Methanosarcina mazei* (SEQ ID No: 3).

FIG. 3. Sequence alignment among WT and mutant *M. mazei* and *M. barkeri* tRNApyl genes (SEQ ID Nos: 72, 3, 73, & 74, respectively)

BRIEF DESCRIPTION OF THE SEQUENCE LISTING

Figure 1A:
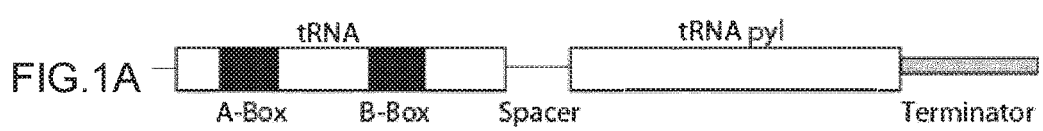
FIG. 1A shows a DNA construct in which a tRNApyl gene is operably linked to a eukaryotic tRNA gene which includes a RNA polymerase III type 2 promoter and expressed as a bicistronic message.
Figure 1B:
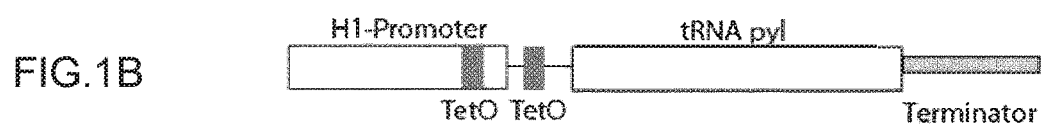
FIG. 1B shows a DNA construct which includes a H1 promoter.

SEQ ID No 1: tRNApyl *Methanosarcina barkeri*, WT
SEQ ID No 2: tRNApyl *Methanosarcina acetivorans*, WT
SEQ ID No 3: tRNApyl *Methanosarcina mazei*, WT
SEQ ID No 4: tRNApyl *Methanococcoides burtonii*, WT
SEQ ID No 5: tRNApyl *Desulfobacterium hafniense*, WT
SEQ ID No 6: Terminator sequence used for WT and mutant A-box and/or B-box tRNApyl constructs
SEQ ID No 7: tRNApyl *Methanosarcina mazei* A10G mutation, tRNA-A1
SEQ ID No 8: tRNApyl *Methanosarcina mazei* A10G, A52C mutations, tRNA-AB
SEQ ID No 9: tRNApyl *Methanosarcina mazei* A52C mutation, tRNA-B
SEQ ID No 10: tRNApyl *Methanosarcina mazei* A10G, T14A, A52C mutations, tRNA-A2B
SEQ ID No 11 tRNApyl *Methanosarcina mazei* A10G, T14A mutation, tRNA-A2
SEQ ID No 12: 7SL Promoter 5' region sequence
SEQ ID No 13: Spacer used in 7SL constructs
SEQ ID No 14: 7SL tRNA-WT construct
SEQ ID No 15: 7SL tRNA-B construct
SEQ ID No 16: 7SL tRNA-A1 construct
SEQ ID No 17: 7SL tRNA-AB construct
SEQ ID No 18: 7SL tRNA-A2B construct
SEQ ID No 19: Terminator sequence used in the 7SL, Vault, EBER constructs
SEQ ID No 20: Vault promoter 5' region sequence
SEQ ID No 21: Spacer used for Vault constructs
SEQ ID No 22: Vault tRNA-WT constructs
SEQ ID No 23: Vault tRNA-B construct
SEQ ID No 24: Vault tRNA-AB construct
SEQ ID No 25; Vault tRNA-A2B construct
SEQ ID No 26: EBER2 Promoter 5' region sequence
SEQ ID No 27: Spacer used in EBER constructs
SEQ ID No 28: EBER2 tRNA-WT constructs
SEQ ID No 29: EBER2 tRNA-B construct
SEQ ID No 30: EBER2 tRNA-A1 construct
SEQ ID No 31: EBER2 tRNA-AB construct
SEQ ID No 32: EBER2 tRNA-A2B construct
SEQ ID No 33: H1 promoter sequence
SEQ ID No 34: H1 tRNA-WT construct
SEQ ID No 35: H1 tRNA-B construct
SEQ ID No 36: H1 tRNA-A1 construct
SEQ ID No 37: H1 tRNA-A2 construct
SEQ ID No 38: H1 tRNA-A2B construct
SEQ ID No 39: Terminator sequence used in the H1-tRNA constructs:
SEQ ID No 40: *M. Musculus* tRNAglu coding sequence
SEQ ID No 41: *M. musculus* tRNAglu coding sequence with upstream and downstream regions
SEQ ID No 42: tRNAglu-tRNApyl DNA construct
SEQ ID No 43: 3×tRNAglu-tRNApyl: DNA construct including 3 repeats of the bicistronic construct.
SEQ ID No 44: Leader sequence for the tRNAglu-pyl constructs
SEQ ID No 45: Terminator sequence used in the tRNAglu-pyl constructs SEQ ID No 46: Terminator sequence used in the tRNAglu-pyl constructs
SEQ ID No 47: Intergene sequence used in the tRNAglu-pyl constructs
SEQ ID No 48: *M. Musculus* tRNAasp coding sequence
SEQ ID No 49: *M. Musculus* tRNAasp coding sequence with upstream and downstream regions
SEQ ID No 50: tRNAasp-pyl DNA construct
SEQ ID No 51: 2×tRNAasp-pyl: DNA construct including 2 repeats of the bicistronic construct
SEQ ID No 52: Leader sequence used in the tRNAasp-pyl construct
SEQ ID No 53: Terminator sequence used in the tRNAasp-pyl construct
SEQ ID No 54: intergene sequence used in the tRNAasp-pyl constructs
SEQ ID No 55: human tRNAglu coding sequence
SEQ ID No 56: human tRNAasp coding sequence
SEQ ID No 57: 7SL promoter variant: 7SL-1
SEQ ID No 58: 7SL promoter variant: 7SL-2
SEQ ID No 59: 7SL promoter variant: SL28
SEQ ID No 60: 7SL promoter variant: 7L63
SEQ ID No 61: 7SL promoter variant: 7L23
SEQ ID No 62: 7SL promoter variant: 7L7
SEQ ID No 63: EBER promoter variant: EBER1
SEQ ID No 64: Vault promoter variant: Hvg3
SEQ ID No 65: Vault promoter variant: Hvg2
SEQ ID No 66: *Methanosarcina mazei* pylRS amino acid sequence
SEQ ID No 67: *Methanosarcina mazei* pylRS nucleotide sequence
SEQ ID No 68: short spacer region
SEQ ID No 69: a DNA construct shown in FIG. 1
SEQ ID No 70: a DNA construct shown in FIG. 1
SEQ ID No 71: a DNA construct shown in FIG. 1
SEQ ID No 72: a DNA sequence shown in FIG. 3
SEQ ID No 73: a DNA sequence shown in FIG. 3
SEQ ID No 74: a DNA sequence shown in FIG. 3
SEQ ID No 75: proximal sequence element of the Vault promoter
SEQ ID No 76: SP1 binding site of the EBER promoter
SEQ ID No 77: ATF binding sequence of the EBER promoter
SEQ ID No 78: ATF or CRE binding site of 7SL promoter
SEQ ID No 79: ETAB sequence of 7SL promoter
SEQ ID No 80: spacer region from SEQ ID No 42
SEQ ID No 81: spacer region from SEQ ID No 50

EMBODIMENTS OF THE INVENTION

According to a first aspect of the invention, there is provided a DNA construct which comprises a tRNApyl coding sequence and a RNA polymerase III promoter sequence which is capable of acting to express functional tRNAPyl sufficiently to support nonsense suppression (particularly amber suppression) in a eukaryotic expression system.

Suitably, the tRNApyl coding sequence of the invention lacks the final three nucleotides, CCA, which are added posttranscriptionally in eukaryotic cells.

Suitably, the DNA construct of the invention comprises a terminator sequence which is downstream of the tRNApyl coding sequence. Suitably, a terminator sequence consists of a run of 4 or more thymidine nucleotides 3' of the tRNA coding sequence that functions as a signal for termination of transcription.

Preferred terminator sequences of the invention are identified as SEQ ID Nos 6, 19, 39, 45, 46 and 53, especially, SEQ ID No. 6.

In an embodiment, a DNA construct of the invention comprise 2 to 60 repeats of a tRNApyl gene. Preferably the DNA construct comprises 2 to 30 repeats, more preferably 8 repeats.

Suitably, the DNA construct of the invention comprises a tRNApyl gene comprising the tRNApyl coding sequence and a functional intragenic RNA polymerase III promoter. Said intragenic RNA polymerase III promoter comprises two components—an A box and a B box.

Suitably, the invention provides a DNA construct wherein the tRNApyl gene contains mutations in 1 or 2 nucleotide positions in the A box and/or the B box of the intragenic RNA polymerase III promoter.

For example, the invention provides a DNA construct wherein the tRNApyl gene contains mutations in 1 or 2 (e.g. 1) nucleotide positions in the B box.

Figure 1C:
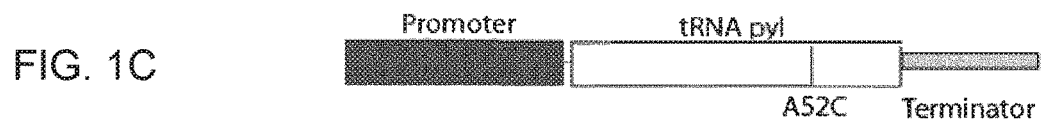
FIG. 1C shows a DNA construct which includes an intragenic promoter element and RNA polymerase III promoter element placed 5' to the tRNApyl coding sequence.
Figure 1D:
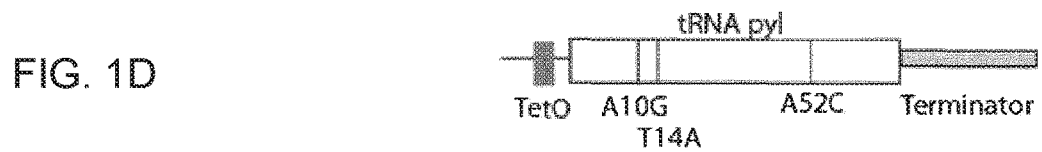
FIG. 1D shows a DNA construct comprising a tRNApyl gene comprising an intragenic PolIII promoter.

In an embodiment of the invention, the DNA construct comprises a tRNApyl gene comprising an intragenic PolIII promoter, e.g. as shown in FIG. 1D, which is capable of acting to express functional tRNAPyl sufficiently to support nonsense suppression in a eukaryotic expression system.

In a preferred embodiment of the invention, there is provided a DNA construct wherein the tRNApyl gene has or comprises a sequence selected from SEQ ID Nos 7, 8, 9, 10 and 11 derived from *Methanosarcina mazei* (especially SEQ ID Nos 9 or 10) or has or comprises the sequence of an analogous tRNApyl gene derived from another bacterial species in which the mutations indicated by bold in SEQ ID Nos 7, 8, 9, 10 or 11 (especially SEQ ID Nos 9 or 10) are made in equivalent positions.

The determination of equivalent positions may be made by conventional alignment programs, e.g. using BLASTN.

Particularly preferred DNA constructs of the present invention comprise a tRNApyl gene of SEQ ID Nos 9 or 10, and a terminator sequence downstream of the tRNApyl coding sequence, which terminator sequence is SEQ ID No 6.

In a further, preferred embodiment, the invention provides a DNA construct comprising multiple copies of the tRNApyl gene comprising an intragenic RNA polymerase III promoter. Preferably the DNA construct comprises 2 to 30 copies, more preferably 8 copies of the tRNApyl gene comprising an intragenic RNA polymerase III promoter.

In an embodiment, the invention provides a DNA construct wherein the tRNApyl coding sequence is operably linked to a RNA polymerase III promoter wherein said promoter is placed 5' to the tRNApyl coding sequence.

Suitably, the 5' promoter and the tRNApyl coding sequence are separated by a spacer sequence containing a transcriptional start site.

Preferably, the spacer sequence contains a transcription start site and 4 to 6 nucleotides from the end of the promoter sequence to the start of the tRNA coding sequence. Preferred spacer sequences to be used in the present invention are listed as SEQ ID NOs 13, 21 and 27.

Suitably a DNA construct comprises an intragenic promoter element and a 5' promoter element being a RNA polymerase III promoter element placed 5' to the tRNApyl coding sequence such that the combination of said intragenic promoter element and said 5' promoter element constitutes a hybrid promoter, e.g. as shown in FIG. 1C.

Suitably, said 5' promoter element is the 5' element of a Type 4 RNA polymerase III promoter. Thus it typically comprises an upstream promoter element typical of the pal III/type 3 class of promoters, for example it comprises a TATA box, (such as one used in a U6 or H1 promoter). Suitably, said intragenic promoter element comprises an element typical of the polIII/type 2 promoters, for example an A- and B-box (e.g. such as used in eukarotic tRNA promoters).

It will be understood that "an element" is not restricted to single nucleotide sequence and can be construed to include more than one nucleotide sequence. Thus for example an A and B box together can represent "an intragenic promoter element". The A and B box may be viewed as separate components of the intragenic promoter element.

Preferably, the 5' promoter element of a Type 4 RNA Polymerase III promoters is selected from 5' promoter elements of the EBER RNA gene promoter, the 7SL RNA gene promoter and the Vault RNA gene promoter, particularly the 7SL RNA gene promoter.

The EBER RNA gene promoter may be, for example EBER variant EBER1 or EBER2, especially EBER2, The 7SL RNA gene promoter may be, for example, variant 7SL-1, 7SL-2, SL28, 7L63, 7L23 or 7L7.

The Vault RNA gene promoter may be, for example, variant Hvg2 or Hvg3.

Preferably, said 5' promoter element is selected from SEQ ID Nos 12, 20, 26, 57, 58, 59, 60, 61, 62, 63, 64 and 65.

Suitably, the 5' promoter element and the tRNApyl coding sequence are separated by a spacer sequence containing a transcriptional start site. Suitably, the spacer sequence contains a transcription start site and 4-6 nucleotides from the end of the promoter sequence to the start of the tRNA coding sequence. Preferred spacer sequences to be used in the present invention are listed as SEQ ID NOs 13, 21 and 27.

Preferably, the Type 4 RNA polymerase III promoters are promoters from eukaryotic genes, more preferably mammalian genes, more preferably, human genes.

Particularly preferred 5' promoter elements are selected from SEQ ID Nos 12, 20 and 26.

In a preferred embodiment of the invention, there is provided a DNA construct which is capable of acting to express functional tRNAPyl sufficiently to support nonsense suppression in a eukaryotic expression system comprising a tRNApyl gene comprising a tRNApyl coding sequence which contains mutations in 1 or 2 nucleotide positions in the putative A box and/or B box of an intragenic promoter element which is operably linked to a 5' promoter element being an RNA polymerase III promoter placed 5' to the tRNApyl gene, and wherein the combination of said intragenic promoter element and said 5' promoter element constitutes a hybrid promoter.

A particularly preferred DNA construct within the context of the present invention comprises a tRNApyl gene comprising a tRNApyl gene coding sequence and an intragenic promoter element wherein said gene has or comprises a sequence selected from SEQ ID No 7, 8, 9, 10 and 11, derived from *Methanosarcina mazei* or has or comprises the sequence of an analogous tRNApyl gene derived from another bacterial species in which the mutations indicated by bold in SEQ ID Nos 7, 8, 9, 10 and 11 are made in equivalent positions, which is capable of acting to express functional tRNAPyl sufficiently to support nonsense suppression in a eukaryotic expression system, wherein the tRNApyl coding sequence is operably linked to a 5' promoter element being an RNA polymerase III promoter element which is placed 5' to the tRNApyl coding sequence, separated by a spacer sequence and wherein the combination of said 5' promoter element and intragenic promoter constitutes a hybrid promoter.

Thus, preferred DNA constructs of the invention are selected from SEQ ID NOs 15, 16, 17, 18, 22, 23, 24, 25, 28, 29, 30, 31 and 32, particularly SEQ ID 15, 16, 17, 18, 23, 25 and 29, especially SEQ ID Nos 15, 18 and 23.

An aspect of the invention provides a multimeric DNA construct comprising multiple copies (e.g. 2 to 60 copies e.g. 2 to 30 copies e.g. 8 copies) of any of the DNA constructs as aforesaid.

Particularly preferred DNA constructs of the invention comprise 8 copies of the tRNApyl gene selected from SEQ ID NOs 15, 16, 17, 18, 22, 23, 24, 25, 28, 29, 30, 31 and 32.

Most preferred tRNApyl genes repeated multiple times in DNA constructs of the present invention are selected from SEQ ID Nos 15, 18 and 23.

In an alternative embodiment, the invention provides a DNA construct wherein a tRNApyl gene is operably linked to a eukaryotic tRNA gene which comprises a RNA polymerase III type 2 promoter and expressed as a bicistronic message e.g. as shown in FIG. 1A.

Suitably, the eukaryotic tRNA gene lacks the 3' terminator sequence, thereby allowing expression of the tRNApyl gene to occur under the control of the eukaryotic RNA polymerase III type 2 promoter.

Preferably, the eukaryotic tRNA gene operably linked to the tRNApyl is tRNAglu or tRNAasp which lead to high level of expression of the tRNApyl More preferably, the eukaryotic tRNA gene operably linked to the tRNApyl gene is a mammalian tRNAglu or a tRNAasp, more preferably murine or human.

Thus the invention provides a DNA construct which comprises a eukaryotic tRNAglu gene or a eucaryotic tRNAasp gene 5' to a tRNApyl gene, said tRNAglu gene or tRNAasp gene being deprived of a termination sequence thus leading to a bicistronic message upon transcription.

The tRNApyl gene may be a wildtype gene. Alternatively, the tRNApyl gene may contain mutations in 1 or 2 nucleotide positions in the A box and/or the B box e.g. as described above.

Suitably, the first tRNA is separated from the second tRNA by a spacer sequence consisting of a sequence devoid of thymidine nucleotides which constitute a signal for termination of transcription.

Preferred spacer sequences are defined in SEQ ID Nos 47 and 54.

Preferably, the eukaryotic tRNA gene operably linked to the tRNApyl gene is a mammalian tRNAglu or a tRNAasp of SEQ ID No 41, 49, 55 or 56; more preferably, a murine tRNAglu or tRNAasp of SEQ ID No 41 or 49.

In an embodiment, a murine tRNAglu or tRNAasp gene is used for expression of the tRNApyl gene in murine cell lines. In an embodiment, a human tRNAglu or tRNAasp gene is used for expression of the tRNApyl gene in murine cell lines In a particularly preferred embodiment of the invention, it is provided a DNA construct wherein the tRNApyl gene is expressed as a bicistronic message of SEQ ID No 42 or SEQ ID No 50.

In a further embodiment, the first tRNA is preceded by a 5' leader sequence that may contain sequence elements such as a TATA box, a transcription start site (TSS), and sequences that regulate the post-transcriptional processing of the pre-tRNA to generate a mature tRNA.

The leader sequence may be selected from untranslated regions upstream of the coding sequence of any mammalian tRNA that is transcribed. Preferably, the leader sequence is selected from SEQ ID Nos 44 and 52. Alternatively, the leader sequence is comprised in the genomic untranslated region 5' to the first tRNA.

Particularly preferred constructs according to the present invention comprise multiple copies (e.g. 2-20 copies) of the bicistronic transcription unit of SEQ ID Nos 42 or 50. Thus, preferred DNA constructs of the present invention comprise, 2, 3, 4, 5, 6, 7 or 8 copies of the transcription unit of SEQ ID Nos 42 or 50. Most preferred DNA constructs according to the present invention are SEQ ID No 43, representing 3 copies of the tRNAglu-pyl bicistronic transcription unit of SEQ ID No 42, and SEQ ID No 51, representing 2 copies of the tRNAasp-pyl bicistronic unit of SEQ ID No 50.

As an aspect of the invention, any of the DNA constructs as aforesaid may comprise a PylRS coding sequence or gene.

According to an aspect of the invention there is provided a eukaryotic host cell which is transformed with a vector comprising a DNA construct as aforesaid.

According to a second aspect of the invention, there is provided a eukaryotic cell line which expresses or is capable of expressing PylRS and tRNApyl, in which tRNApyl is introduced into the cells with DNA constructs of the invention and which functions in said eukaryotic cell line.

According to a third aspect of the invention, there is provided a cell-free expression system wherein a synthesis reaction lysate obtained from a host cell comprises at least one component required for the synthesis of polypeptides.

Suitably, the synthesis reaction lysate is obtained from bacterial or eukaryotic cells. Preferably, the synthesis reaction lysate is obtained from eukaryotic cells, more preferably, from rabbit reticulocytes or wheat germ.

Preferably, the cell-free expression system is capable of expressing WT PylRS and tRNApyl of the present invention, wherein tRNApyl is introduced into the cells used to obtain the synthesis reaction lysate with DNA constructs of the invention.

Cell-free expression systems suitable for use in the present invention are described for instance in WO201008110, WO2010081111, WO2010083148, incorporated in their entirety herein by reference.

A eukaryotic host cell according of the invention may be transformed with a vector comprising a gene encoding a target protein containing one or more non-natural amino acids encoded by a nonsense codon.

In an embodiment, a eukaryotic cell line expresses or is capable of expressing functional PylRS and functional tRNApyl in which functional tRNApyl expression occurs under the control of a an intragenic promoter element and a 5' promoter element being a RNA polymerase III promoter element placed 5' to the tRNApyl coding sequence such that the combination of said intragenic promoter element and said 5' promoter element constitute a hybrid promoter sufficiently to support nonsense suppression.

Suitably the nonsense suppression is amber suppression.
Suitably the host cell is a mammalian cell.

In a fourth aspect, the invention provides a process for preparing a target protein containing one or more non-natural amino acids encoded by a nonsense codon which comprises expressing said target protein in a eukaryotic cell line which is transformed with a gene encoding a target protein containing one or more non-natural amino acids encoded by a nonsense codon and which is also transformed with genes encoding PylRS and tRNApyl, such that PylRS and tRNApyl are expressed and function in said eukaryotic cell line sufficiently to support nonsense suppression.

Suitably the cell line is transformed with a DNA construct according to other aspects of the invention described herein.

Thus, the nonsense codon utilized in the embodiments of the invention might be an amber codon, an opal codon, or an ochre codon. A particularly preferred nonsense codon is an amber codon.

The invention provides a process for preparing a chemically modified target protein which comprises preparing a target protein according to an above aspect of the invention and chemically modifying the resultant target protein. The protein may be chemically modified via a side chain on a non natural amino acid.

Thus, the non-natural amino acids utilized in embodiments of the present invention, or at least one of them, may comprise an alkyne or azide moiety. These moieties are well adapted for chemical modification e.g. via the Huisgen reaction leading to generation of a triazole linker moiety.

In an fifth aspect of the present invention, there is provided a protein conjugate such as an antibody conjugate prepared using a process according to processes of the present invention in which the protein such as an antibody is conjugated to one or more other moieties selected from protein, drug and PEG moieties via linkers comprising a triazole moiety.

In a sixth aspect the present invention provides a process for increasing the viability of a eukaryotic cell line stably transformed to express PylRS and tRNApyl which comprises transforming the eukaryotic cell line with a tRNApyl gene which is introduced into the cells with DNA constructs of the invention and which functions in said eukaryotic cell line, in order to express a target protein containing one or more non-natural amino acids.

In a seventh aspect the present invention provides a process for increasing the viability of a eukaryotic cell line stably transformed to express a target protein containing one or more non-natural amino acids and to express PylRS and tRNApyl which comprises transforming the eukaryotic cell line with genes encoding PylRS and tRNApyl such that PylRS and tRNApyl are expressed and function sufficiently to support nonsense suppression.

Definitions and Abbreviations

As used herein, "gene" means a locatable region of genomic sequence, corresponding to a unit of inheritance, which is associated with regulatory regions, transcribed regions, and or other functional sequence regions. Thus a gene will include a coding sequence (e.g. a coding sequence for an RNA such as a tRNA) together with regulatory regions including promoter elements.

As used herein, "intragenic promoter" means a promoter contained within the gene sequence.

As used herein, a "transcribed region" includes both a coding sequence, i.e. a sequence which is part of the mature RNA product, and portions of the primary transcript that are removed and thus do not appear in the mature RNA, such as the 5' leader portion of tRNA precursors.

As used herein "promoter element" means an element of a promoter, especially of a hybrid promoter that may have a number of elements (e.g. an intragenic promoter element and a 5' promoter element). As used herein, "Type 4 RNA polymerase III promoter" means an RNA polymerase III promoter having an upsteam promoter element or elements (e.g. typical of the type 3 class of RNA polymerase III promoters, for example a TATA box used in U6 or H1 promoters) and an intragenic promoter element or elements (e.g. typical of the type 2 class of RNA polymerase III promoters, for example an A and B box, for example as used in tRNA promoters).

As used herein, a TATA box is a DNA sequence typically containing the sequence TATAAA or a variant thereof found in the promoter region of certain genes, located upstream of the transcription start site.

As used herein, a "nonsense codon" means an amber, ochre or opal codon.

As used herein "nonsense suppression" means suppression of chain termination by a nonsense codon.

As used herein, "nnAA" or "non-natural amino acid" means a amino acid which is suitable for incorporation into proteins and is not one of the 20 amino acids naturally coded for by the genetic code, Pyrrolysine and Selenocysteine.

As used herein, "WT" means wild type i.e. a form naturally obtained in nature.

As used herein, "RS" is an abbreviation for "tRNA synthase".

As used herein, "TSS" is an abbreviation for "transcription start site".

As used herein, "CPE" is an abbreviation for "cyclic AMP response element".

As used herein, "PSE" is an abbreviation for "proximal sequence element".

As used herein, "CHO" is an abbreviation for "Chinese hamster ovary".

As used herein a "coding sequence" is the nucleotide sequence of a gene which codes for the gene product (tRNA, RS etc) and does not include non-coding sequences, such as regulatory sequences.

As used herein, there may be transcribed sequences which are part of the primary transcript but not of the mature RNA, and are therefore considered "non-coding".

As used herein, a "DNA construct" means an artificially constructed segment of nucleic acid to be introduced into an expression system. A DNA construct typically includes an expression cassette and may also contain nucleotides belonging to the vector system used to introduce the nucleic acid into the expression system.

As used herein, an "expression cassette" means an artificially constructed segment of nucleic acid to be introduced into an expression system which comprises one or more gene-coding sequences such as cDNA or RNA coding sequences, along with any necessary regulatory regions for optimal expression. An expression cassette does not contain nucleotides belonging to the vector system.

As used herein, a "bicistronic" transcript is a transcript with the potential to code for two final products.

DETAILED DESCRIPTION tRNApyl to be Expressed in Cell Lines According to the Invention The tRNApyl to be expressed in combination with the PylRS of the present invention has an anticodon and a tertiary structure which are complementary to the amber nonsense codon UAG, in order to function as a suppressor tRNA.

An artificial tRNA could be constructed that is complementary to other nonsense codons such as UGA, opal; UAA, ochre codons in order to function as a suppressor tRNA.

Thus it will be understood that although the present invention is substantially described and exemplified by reference to use of the amber codon for coding the nnAA and with discussion of the concept of amber suppression, the amber codon can be replaced with an another nonsense codon such as opal or ochre codons and would be expected to work in the same way.

However use of amber codon is preferred.

Preferably, the tRNApyl of the present invention is a tRNApyl derived from one of the following bacterial strains: *Methanosarcina mazei* (SEQ ID No 3), *Methanosarcina barkeri* (SEQ ID No 1), *Desulfitobacterium hafniense* (SEQ ID No 5), *Methanosarcina acetivorans* (SEQ ID No 2), *Methanosarcina burtonii* (SEQ ID No 4), or *Methanosarcina thermophila*.

More preferably, the tRNApyl of the present invention is a tRNApyl derived from *Methanosarcina mazei* (SEQ ID No 3)

Suitably, the tRNApyl of use in aspects of the present invention is not a tRNApyl derived from *Methanosarcina barkeri* (SEQ ID No 1)

Engineering of tRNApyl sequences in order to optimize expression in eukaryotic cell lines has been described in WO2007099854, WO12038706, and Hancock et al (2010) incorporated herein by reference.

WO2007099854 provides inter alia DNA constructs comprising a tRNA coding sequence deriving from Archaebacteria, preferably tRNApyl, a transcription terminator sequence placed 3' of said tRNA gene, a promoter sequence that induces transcription by RNA Polymerase II or III such as U1 snRNA promoter or U6 snRNA promoter placed 5' to said tRNApyl coding sequence.

WO12038706 provides inter alia DNA constructs comprising tRNApyl from *Methanosarcina barkeri* operably linked to a RNA polymerase III promoter, in particular linked to the RNA polymerase III promoter of a yeast tRNAarg gene.

WO12038706 further provides DNA constructs for expression in yeast cells, comprising tRNApyl from *Methanosarcina barkeri* mutated at several internal positions, summarized in FIG. 3. Interestingly, *M. Barkeri* tRNApyl differs by one nucleotide from *M. mazei* tRNApyl, corresponding to nucleotide G at position 3 of SEQ ID No. 3 tRNApyl with Intragenic polIII Promoter

A tRNApyl gene included in DNA constructs of the present invention may comprise an intragenic polIII promoter.

Hancock et al (2010) described DNA constructs for expression of tRNApyl in yeast cells, comprising tRNApyl from *Methanosarcina barkeri* mutated at several internal positions, summarized in FIG. 3. In yeast, the introduction of a mutation in the B-box resulted in the generation of the consensus B box sequence, and led to very low but detectable levels of the mutant tRNApyl expression. However, expression of the mutant tRNApyl did not support amber suppression in the yeast cells. The authors concluded that either the tRNA was improperly folded or processed, or that the mutation abolished synthetase recognition.

Similarly, the authors recreated a near-consensus A box which expression was not detectable and they combined the A-box and B-box mutations which led to detectable expression levels but no amber suppression.

In particular, the mutations generated by Hancock et al in the *M. Barkeri* tRNApyl gene correspond to *M. mazei* position 10, 14, 25, and 52. Interestingly, wild type *M. Barkeri* tRNApyl differs by one nucleotide from *M. mazei* tRNApyl, corresponding to nucleotide G at position 3 of SEQ ID No. 1

Surprisingly, the inventors have now discovered that introduction of certain mutations in the putative A-box and B-box regions of the *M. mazei* tRNApyl gene does result in successful expression of tRNApyl in mammalian cells, associated with efficient amber suppression.

The inventors have recreated a consensus B box and a near-consensus A box which function both in combination and separately to allow amber suppression, as discussed in Example 1 and FIGS. 4-7.

Suitably, the B box mutation is A52C referred to the WT sequence of SEQ ID 3.

Suitably, the A box mutation comprises two mutations which have been analysed together and separately and determined to lead to amber suppression in mammalian cells, corresponding to positions 10 and 14 referred to the WT sequence of SEQ ID No 3.

Exemplary tRNApyl mutant genes of SEQ ID Nos 7, 8, 9, 10 or 11 (corresponding to mutated sequences from the tRNApyl gene of *Methanosarcina mazei*) and analogous tRNApyl genes derived from other bacterial species (e.g. those mentioned above) in which a mutation (indicated by bold in SEQ ID Nos 7, 8, 9, 10, and 11) is made in an equivalent position. The mutations may, for example, be 1 or 2 nucleotide positions in the putative A box and/or the putative B box. For example a single mutation is made in the putative B box e.g. in the position shown in SEQ ID Nos 7, 8, 9, 10 or 11. For example a single or two mutations are made in the putative A box and a single mutation is made in the B box e.g. in the positions shown in SEQ ID No. 7-11. The putative A and B boxes are shown in FIG. 2 and the skilled person can derive the putative A and B boxes regions for analogous tRNApyl genes derived from other bacterial species (e.g. those mentioned above).

Suitably, the DNA constructs of the present invention comprise a mutated tRNApyl gene followed by a terminator sequence. An exemplary terminator sequence is listed in SEQ ID 6

The proper folding of the tRNA is highly sensitive to any modification of its sequence. Surprisingly, the mutations in equivalent positions in the tRNA from *M. barkeri* and *M. mazei* has led to dramatically different results as shown in WO2012/038706 and in the examples of the present invention. Notably, the *M. barkeri* tRNApyl gene has a different nucleotide at position 3 (G) compared to the *M. mazei* tRNA where at the equivalent position there is an A.

It has been hypothesized that the G at position 3 decreased efficacy of RS aminoacylation, and that G at position 3 affects orthogonality of the tRNApyl in yeast. (Hancock 2010; Gundllapalli et al 2008).

Briefly, the recognition of specific tRNAs by the Aminoacyl tRNA synthetases and the tRNA aminoacylation occurs through identity elements specified by the tRNA sequence. The acceptor stem consists of 7 nucleotide pairs formed by the 3' and 5' terminal ends of the tRNA and is important for the recognition of tRNA by enzymes and critical in translation. The tRNApyl of *M. barkeri* Fusaro contains an unusual G3:70U base pair in the acceptor stem region that is not found in other tRNApyl genes. This mutation was shown to affect the orthogonality of the tRNA in yeast by allowing misacylation of the tRNApyl by the yeast seryl tRNA synthetase.

As a further comment to the regulation of expression of polIII dependent genes can vary between yeast and mammalian cells. In both, tRNAs are governed by intragenic A and B-box elements, but extragenic sequences can affect the expression level, transcription start site (TSS) and the processing of pre-tRNA. In yeast, the TSS is frequently found 18-20 bp upstream of the T marking the first base of the A-box (or 10-12 bp upstream of the start of mature tRNA coding sequence). In addition, in yeast the TSS is often surrounded by a core promoter element tCAAca (where the capital letters indicate high conservation).

Figure 7:
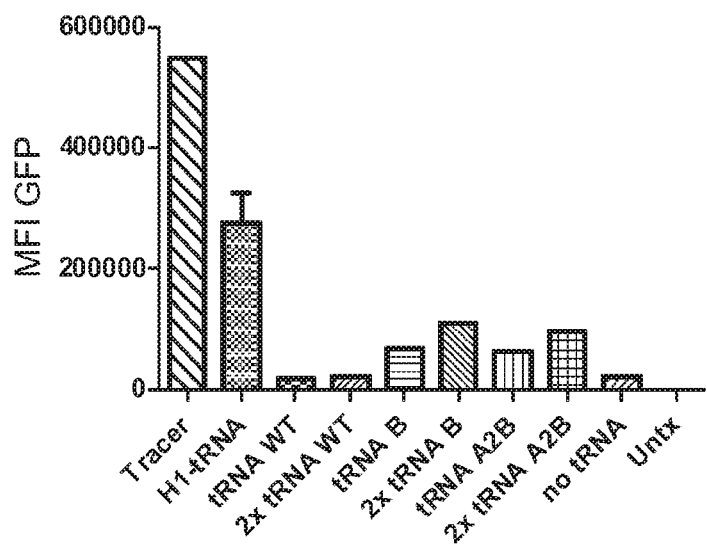

Surprisingly, the inventors have also found that DNA constructs built by assembling a series of repeats of the mutant tRNA genes of the invention provide enhanced expression and amber suppression, as exemplified in FIG. 7 and Example 2

Suitably, DNA constructs of the invention comprise 2 to 60 repeats of a tRNApyl gene. Preferably the DNA construct comprises 2 to 30 repeats, more preferably 8 repeats.

tRNApyl with Intragenic polIII Promoter Expressed Under 5' Promoter Elements

The lack of success in producing a functional amber suppressor by enhancing the transcription of a functional tRNApyl by mutation of the A- and B-box sequences within the structural gene, led investigators in the field to engineering of DNA constructs wherein the transcription of the tRNApyl gene would be increased using only extragenic sequences, as reported above.

The inventors have now engineered a novel and improved promoter element which combines upstream promoter elements and intragenic promoter elements.

Certain eukaryotic RNA genes are expressed under a hybrid polymerase III promoter, or type 4 promoter, comprising upstream promoter elements typical of the pol III/type 3 class of promoters (eg TATA box, used in U6 or H1 promoter), or also possibly comprising sequences unrelated to type 3 promoter sequences, and intragenic promoter elements typical of the polIII/type 2 promoters (eg A- and B-boxes, used in tRNA promoters).

Suitably, upstream promoter elements utilized in the invention are selected from promoters of 7SL (SRP) RNA gene, Vault RNA gene, Epstein Barr virus coded small RNA (EBER) identified in SEQ ID Nos 12, 20, 26, 57, 58, 59, 60, 61, 62, 63, 64 or 65.

Suitably, upstream promoter elements of the invention are isolated from mammalian genes, preferably human or murine genes, most preferably human as in SEQ ID Nos 12, 20 or 26.

Suitably, the promoter sequences contain functional elements that recruit transcription factors that regulate transcription by PolIII RNA polymerase as shown in FIG. 1E (SEQ ID Nos: 69-71).

Hence, the 7SL promoter contains an Activating transcription factor (ATF) or cyclic AMP response element (CRE) binding site (tgacgtcac) SEQ ID NO:78 located 43-51 bp upstream of the transcription start site. The promoter also contains a TATA—like sequence called an ETAB sequence (ttctagtgct) SEQ ID NO:79 20-31 bp upstream of TSS.

The Vault promoter contains a proximal sequence element (PSE) located 23-53 bp upstream of the TSS (tgacgtaggtctttctcaccagtca) (SEQ ID No: 75) and is also a variant of the cyclic AMP response element (CRE). In addition the Vault promoter contains a TATA box (tataat) 16-22 bp upstream of the TSS.

The EBER promoter contains three regulatory regions, a SP1 binding site (gcacgcttaacccgcctaca) (SEQ ID No: 76) 76-55 bp upstream of the TSS, an ATF binding sequence (accgtgacgtagctgttta) (SEQ ID No: 77) 55-36 bp upstream of the TSS, and a TATA-like box (tatagag) 28-21 bp upstream of the TSS.

Figure 8:
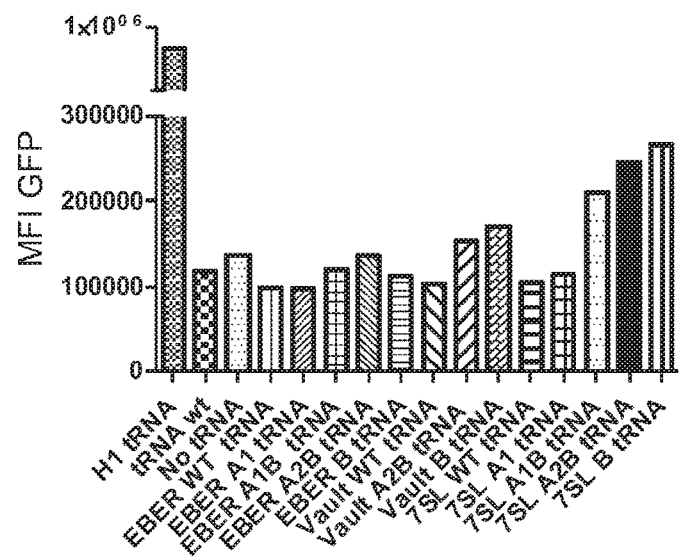

In the context of the present invention, the combination of upstream promoter elements of the 7SL, EBER, Vault RNAs with the reconstituted intragenic promoter (A- and/or B-box) within the tRNApyl gene has proven to improve the amber suppression function of such tRNA, over the tRNApyl containing the reconstituted intragenic promoter alone, and over the WT tRNApyl, as shown in FIG. 8 and example 3.

Suitably, the 7SL promoter of SEQ ID No 12 is combined with the B-box mutation of SEQ ID No 9, as in the construct of SEQ ID No 15.

Alternatively, the 7SL promoter of SEQ ID No 12 is combined with the A- and B-box mutation of SEQ ID No 10, as in the construct of SEQ ID No 18.

Preferred DNA constructs of the present invention comprise an upstream promoter element, separated by the transcription start site by a spacer. Suitably, the spacer sequence contains a transcription start site and 4-6 nucleotides from the end of the promoter sequence to the start of the tRNA coding sequence.

DNA constructs of the invention comprise a downstream termination site, placed 3' of the tRNApyl coding sequence, wherein said termination site signals termination of polymerase III transcription through a small poly-thymidine (4-6) sequence. Preferred terminator sequence of the invention is listed as SEQ ID No 19.

tRNApyl Expressed Under Eukaryotic tRNA Genes as Bicistronic Messages

Mukai et al, 2008 and EP1992698 describe how the tRNApyl gene downstream to a eukaryotic tRNA (tRNAval) gene led to a suboptimal expression of tRNApyl, not ideal as levels of expression were too low for optimal amber suppression in mammalian cells.

Figure 11:
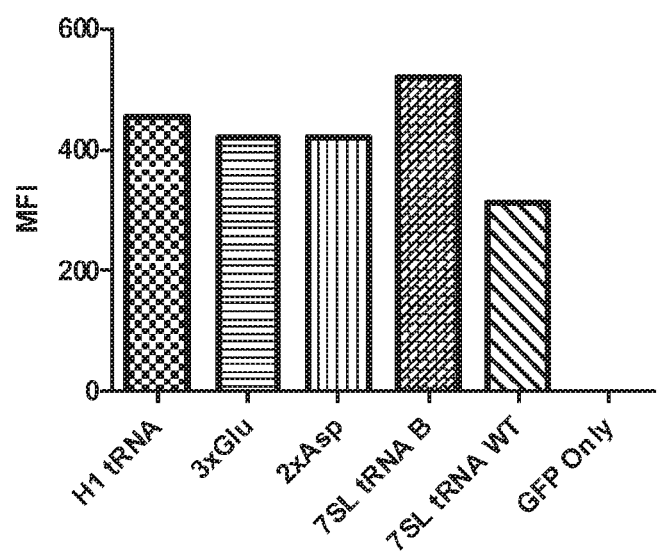

The present inventors have surprisingly found DNA constructs wherein the tRNApyl coding sequence is operably linked to a eukaryotic tRNA gene such as tRNAglu or tRNAasp (FIG. 1A) lead to optimal expression of the tRNApyl gene product as well as amber suppression, as described in detail in FIG. 11 and example 4

Suitably, the tRNApyl gene of the present invention is expressed as a bicistronic message in a eukaryotic host cell.

Suitably, the eukaryotic tRNA gene lacks the 3' terminator sequence, thereby allowing expression of the tRNApyl gene to occur under the eukaryotic RNA polymerase III type 2 promoter.

Hence, the first tRNA is separated from the second tRNA by a spacer sequence consisting of a sequence devoid of Thymidine nucleotides which constitute a signal for termination of transcription.

Exemplary spacer sequences are shown in SEQ ID Nos 47 and 54.

Preferably, the eukaryotic tRNA gene operably linked to the tRNApyl coding sequence is a mammalian tRNAglu or a tRNAasp gene, of SEQ ID No 41, 49, 55 or 56; more preferably, a murine tRNAglu or tRNAasp of SEQ ID No 41 or 49.

The inventors have surprisingly found that expression of the tRNApyl and amber suppression are particularly efficient when the first tRNA gene is preceded by a 5' leader sequence that contains sequence elements such as a TATA box, a transcription start site (TSS), and sequences that regulate the post-transcriptional processing of the pre-tRNA to generate a mature tRNA, collectively referred to as leader sequence.

Hence, the leader sequence is the 5' region of any mammalian tRNA gene that is transcribed to generate a portion of tRNA precursor that will not be part of the mature tRNA.

Particularly preferred leader sequences used in the present invention are disclosed in SEQ ID No 41 and 49 and listed as SEQ ID No 44 (tRNAasp) and SEQ ID No 52 (tRNAglu).

Particularly preferred DNA constructs of the invention are listed as SEQ ID No 42 and SEQ ID No 50.

SEQ ID No 42 consists of the murine tRNAglu gene followed by a spacer region (ccccaaacctc) SEQ ID NO:80 devoid of Thymidines, linked to the tRNApyl gene. Thus, the construct of SEQ ID No 42 is transcribed as a single entity that is postrascriptionally processed to generate a mature tRNApyl.

SEQ ID No 50 consists of the murine tRNAasp gene followed by a spacer region (tagccccacctc) SEQ ID NO:81 devoid of Thymidines, linked to the tRNApyl gene. Thus, the construct of SEQ ID No 50 is transcribed as a single entity that is postrascriptionally processed to generate a mature tRNApyl.

Particularly preferred DNA constructs of the present invention comprise multiple copies of the bicistronic transcription unit of SEQ ID Nos 42 and 50.

Thus, particularly preferred DNA constructs comprise, 2, 3, 4, 5, 6, 7, 8, copies of the transcription unit of SEQ ID Nos 42 or 50. Most preferred DNA constructs are SEQ ID No 43, representing 3 copies of the tRNAglu-pyl bicistronic transcription unit of SEQ ID No 42, and SEQ ID No 51, representing 2 copies of the tRNAasp-pyl bicistronic unit of SEQ ID No 50.

The tRNApyl genes of the invention can be introduced into eukaryotic cell lines. Suitably the cell lines are mammalian cell lines.

More preferably, the cell line is a CHO cell line, but also may be a HEK293, PERC6, COS-1, HeLa VERO, or mouse hybridoma cell line.

CHO and HEK293 cells lines are particularly suitable.

PylRS

Suitably, the tRNApyl genes of the present invention are introduced into eukaryotic cell lines in association with pylRS genes.

As used herein, pylRS relates to an amino acyl tRNA synthetase which will aminoacylate a suitable tRNA molecule with pyrrolysine or a derivative thereof.

The pylRS of the present invention is suitably a Pyrrolysyl-tRNA Synthetase orthogonal in eukaryotic cells which is derived from methanogenic *archaea* spp.—i.e. it is wild-type in methanogenic *archaea* spp. or is a mutant thereof.

Preferably, the pylRS of the present invention is a Pyrrolysyl-tRNA Synthetase derived from one of the following: *Methanosarcina mazei, Methanosarcina barkeri, Desulfitobacterium hafniense, Methanosarcina acetivorans, Methanosarcina burtonii, Methanosarcina thermophila, Methanosalsum zhilinae, Methanohalobium evastigatum, Methanohalophilus mahii, Desulfotomaculum gibsoniae, Desulfosporosinus meridei* and *Desulfotomaculum acetoxidans.*

Most preferably, the pylRS of the present invention is the pyrrolysyl tRNA synthetase (pylRS) derived from *Methanosarcina mazei*

The pylRS of the present invention may be a wild type synthetase.

Alternatively, the pylRS of the present invention may be mutated at one or more positions e.g. in order to increase its catalytic activity and/or to modify its selectivity for substrate amino acids (See for instance Yanagisawa 2008).

Preferably, the pylRS of the present invention may be mutated at position corresponding to Tyr 384 of or its equivalent. Most preferably, Tyr 384 is mutated into Phenylalanine.

In one embodiment, the pylRS of the present invention may be mutated at one or more positions in order to modify its substrate specificity and allow (or improve) incorporation of pyrrolysine analogs Further mutant PylRS enzymes are described in WO09038195 and in WO2010114615, each document incorporated herein by reference in its entirety.

Incorporation of Non-Natural Amino Acids Encoded for by Nonsense Codon

In proteins prepared using cell lines of the invention, one or more nnAAs may be incorporated. Suitably one nnAA is incorporated into a protein chain. In the case of the protein being an antibody, one nnAA may be incorporated into the light chain or the heavy chain or both.

In other embodiments more than one e.g. up to four e.g. two (or perhaps three) nnAAs may be incorporated into a protein chain. Suitably all the incorporated nnAAs are the same.

nnAAs are suitably encoded by an amber codon.

Non-Natural Amino Acids that May be Encoded by Amber Codon for Incorporation into Target Proteins Non-Natural Amino Acids for Incorporation into Target Proteins The use of non-natural amino acids to allow for conjugating moieties to peptides is disclosed in WO 2007/130453, incorporated herein by reference.

As used herein a "non-natural amino acid" refers to any amino acid, modified amino acid, or amino acid analogue other than selenocysteine, pyrrolysine, and the following twenty alpha-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine. The generic structure of an alpha-amino acid is illustrated by Formula I:

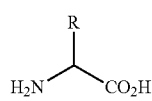

Formula I

A non-natural amino acid is typically any structure having Formula I wherein the R group is any substituent other than one used in the twenty natural amino acids. See, e.g., any biochemistry text such as Biochemistry by L. Stryer, 3rd ed. 1988, Freeman and Company, New York, for structures of the twenty natural amino acids. Note that the non-natural amino acids disclosed herein may be naturally occurring compounds other than the twenty alpha-amino acids above. Because the non-natural amino acids disclosed herein typically differ from the natural amino acids in side chain only, the non-natural amino acids form amide bonds with other amino acids, e.g., natural or non-natural, in the same manner in which they are formed in naturally occurring proteins. However, the non-natural amino acids have side chain groups that distinguish them from the natural amino acids. For example, R in Formula I optionally comprises an alkyl-, aryl-, aryl halide, vinyl halide, alkyl halide, acetyl, ketone, aziridine, nitrile, nitro, halide, acyl-, keto-, azido-, hydroxyl-, hydrazine, cyano-, halo-, hydrazide, alkenyl, alkynyl, ether, thioether, epoxide, sulfone, boronic acid, boronate ester, borane, phenylboronic acid, thiol, seleno-, sulfonyl-, borate, boronate, phospho, phosphono, phosphine, heterocyclic-, pyridyl, naphthyl, benzophenone, cycloalkynes such as the constrained ring such as a cyclooctyne, cycloalkenes such as a norbornenes, transcycloalkenes, cyclopropenes, tetrazines, pyrones, thioester, enone, imine, aldehyde, ester, thioacid, hydroxylamine, amino, carboxylic acid, alpha-keto carboxylic acid, alpha or beta unsaturated acids and amides, glyoxyl amide, or organosilane group, or the like or any combination thereof.

In addition to non-natural amino acids that contain novel side chains, non-natural amino acids also optionally comprise modified backbone structures, e.g., as illustrated by the structures of Formula II and III:

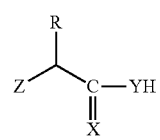

Formula II

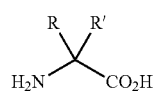

Formula III wherein Z typically comprises OH, $NH_2$, SH, $NH_2O-$, $NH-R'$, $R'NH-$, $R'S-$, or $S-R'-$; X and Y, which may be the same or different, typically comprise S, N, or O, and R and R', which are optionally the same or different, are typically selected from the same list of constituents for the R group described above for the non-natural amino acids having Formula I as well as hydrogen or $(CH_2)_x$ or the natural amino acid side chains.

Other examples of amino acid analogs include (but are not limited to) a non-natural analog of a Lysine or Pyrrolysine amino acid which include one of the following functional groups; an alkyl, aryl, acyl, azido, nitrile, halo, hydrazine, hydrazide, hydroxyl, alkenyl, cycloalkenes, alkynl, cycloalkynes, cycloalkynes such as the constrained ring such as a cyclooctyne, cycloalkenes such as a norbornenes, transcycloalkenes, cyclopropenes, aryl halide, vinyl halide, alkyl halide, aziridine, nitro, hydroxyl, ether, epoxide, vinyl ethers, silyl enol ethers, thiol, thioether, sulfonamide, sulfonyl, sulfone, seleno, ester, thioacid, boronic acid, boronate ester, borane, phosphono, phosphine, heterocyclic, pyridyl, naphthyl, benzophenone, tetrazines, pyrones, enone, imine, aldehyde, hydroxylamine, keto, thioester, ester, thioacid, organosilane group, amino, a photoactivatable cross-linker; a spin-labeled amino acid; a fluorescent amino acid; an amino acid that covalently or noncovalently interacts with another molecule; a metal binding amino acid; a metal-containing amino acid; a radioactive amino acid; a photocaged amino acid; a photoisomerizable amino acid; a biotin or biotin-analogue containing amino acid; a glycosylated or carbohydrate modified amino acid; a keto containing amino acid; an amino acid comprising polyethylene glycol; an amino acid comprising polyether; a heavy atom substituted amino acid; a chemically cleavable or photocleavable amino acid; an amino acid with an elongated side chain; an amino acid containing a toxic group In an embodiment of the present invention, non natural amino acids (nnAA) of the general structure below are utilized for the production of proteins:

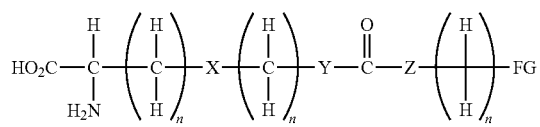

Preferably, the X group can be a methylene group, alkene, arene, oxygen, sulfur, phosphorus, nitrogen, ester, amide, carbonate, carbamate, ether, amine, thioether, alkyne, and heterocycle.

Preferably, the Y group can be a methylene, alkene, arene, oxygen, sulfur, phosphorus, nitrogen, ester, amide, carbonate, carbamate, ether, amine, thioether, alkyne, and heterocycle.

Preferably, the Z group can be a nitrogen, oxygen, sulfur, phosphorus, α-methyleneamino, α-hydroxylamino, α-methyleneazido.

The FG group can be an alkyl azide, alkyl-alkyne, alkyl-alkene, alkyl cyclohexene, alkyl cycloalkyne, alkyl aryl halide, aryl halide, amido cycloalkyne, amido cycloalkene, transcycloalkene, cyclopropenes, tetrazines, pyrones, norbornenes, aryl azide, azido, a hydroxyl amine, a hydrazide, a vinyl halide, a aryl halide, a tetrazine, a pyrone, a imine, boronic ester or acid, a cyano, a carbonyl group such as an aldehyde or ketone.

In a preferred embodiment, non natural amino acids (nnAA) of the general structure above can have methylene groups of varying length in which n=1-12. Preferably, non natural amino acids (nnAA) of the general structure above can contain cycloalkanes and aromatic rings as part of the connective structure.

Suitably, nnAAs of the present invention are derived from lysine as listed in the structure tables below. Those that are not commercially available are optionally synthesized as provided in the examples of US 2004/138106 A1 (incorporated herein by reference) or using standard methods known to those of skill in the art. For organic synthesis techniques, see, e.g., Organic Chemistry by Fessendon and Fessendon, (1982, Second Edition, Willard Grant Press, Boston Mass.); Advanced Organic Chemistry by March (Third Edition, 1985, Wiley and Sons, New York); and Advanced Organic Chemistry by Carey and Sundberg (Third Edition, Parts A and B, 1990, Plenum Press, New York), and WO 02/085923, all of which are hereby incorporated by reference.

nnAAs of the invention may be synthesized by published methods. For instance, synthesis of (S)-2-amino-6((prop-2-ynyloxy)carbonylamino)hexanoic acid and S)-2-amino-6 ((2azidoethoxy)carbonylamino)hexanoic acid is published in WO2010139948 and Nguyen et al. 2009, incorporated herein by reference.

Suitably, nnAAs of the present invention are derived from lysine as shown in the table below as described in part in WO2010139948, incorporated herein by reference.

| Lysine based analogs | |
|---|---|
| Structure | Name |
| [structure] | (2S)-2-amino-6{[(2-azidoethoxy)carbonyl]amino}hexanoic acid |
| [structure] | (2S)-2-amino-6-{[(prop-2-yn-1-yloxy)carbonyl]amino}hexanoic acid |
| [structure] | (2S)-2-amino-6-{[(prop-2-en-1-yloxy)carbonyl]amino}hexanoic acid |
| [structure] | (2S)-2-amino-6-{[(3-azidopropoxy)carbonyl]amino}hexanoic acid |

Suitably, nnAAs of the present invention are derived from (2S)-2-amino-6-hydroxyhexanoic acid as listed in the table below.

| 6-Hydroxy Leucy based analogs | |
|---|---|
| Structure | Name |
| [structure] | (2S)-2-amino-6-{[(2-azidoethyl)carbamoyl]oxy}hexanoic acid |
| [structure] | (2S)-2-amino-6-{[(prop-2-yn-1-yl)carbamoyl]oxy}hexanoic acid |
| [structure] | (2S)-2-amino-6-{[(prop-2-en-1-yl)carbamoyl]oxy}hexanoic acid |

Suitably, nnAAs of the present invention are derived to include different functional groups listed in the table below. Some of which are described in part in WO20110442255A1, incorporated herein by reference.

| Pyrrolysine Analogs | |
|---|---|
| Structure | Name |
| [structure] | (2S)-2-amino-6-(pent-4-enamido)hexanoic acid |

| Pyrrolysine Analogs | |
|---|---|
| Structure | Name |
|  | (2S)-2-amino-6-({[(4-iodophenyl)methoxy]carbonyl}amino)hexanoic acid |
|  | (S)-2-amino-6((2-oxo-2-phenylacetamide)hexanoic acid |
|  | (S)-2-amino-6((2-oxo-2-propanamide)hexanoic acid |
|  | (2S)-2-amino-6-({[(2-ethynylcyclopentyl)oxy]carbonyl}amino)hexanoic acid |
|  | (2S)-2-amino-6-({[(2-azidocyclopentyl)oxy]carbonyl}amino)hexanoic acid |

Suitably, nnAAs of the present invention are derived to include different functional groups suitable for metal free cycloaddition chemistry and are described in part in WO2012104422A1 and listed in the table below.

| Pyrrolysine Analogs | |
|---|---|
| Structure | Name |
|  | (2S)-2-amino-6-[({bicyclo[6.1.0]non-4-yn-9-ylmethoxy}carbonyl)amino]hexanoic acid |
|  | (2S)-2-amino-6-[({bicyclo[6.1.0]non-4-yn-9-ylmethyl}carbamoyl)oxy]hexanoic acid |
|  | (2S)-2-amino-6-{[(cyclooct-2-yn-1-yloxy)carbonyl]amino}hexanoic acid |

TABLE -continued

Pyrrolysine Analogs

| Structure | Name |
|---|---|
| 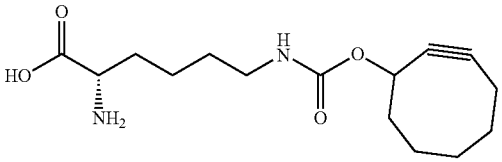 [SMILES: N[C@@H](CCCCNC(=O)OC1C#CCCCCC1)C(=O)O] | (2S)-2-amino-6-({[2-(cyclooct-2-yn-1-yloxy)ethoxy]carbonlyl}amino)hexanoic acid |
| 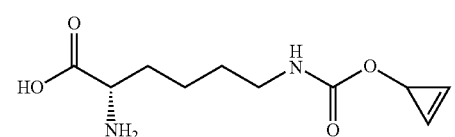 | (2S)-2-amino-6-{[(cycloprop-2-en-1-yloxy)carbonyl]amino}hexanoic acid |
| 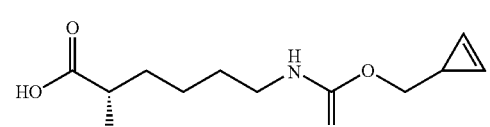 | (2S)-2-amino-6-{[(cycloprop-2-en-1-ylmethoxy)carboxy]amino}hexanoic acid |
| 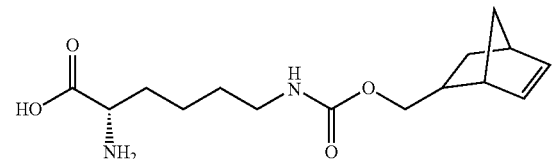 | (2S)-2-amino-6-[({bicyclo[2.2.1]hept-5-en-2-ylmethoxy}carbonyl)amino]hexanoic acid |
| 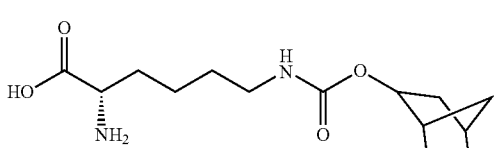 | (2S)-2-amino-6-[({bicyclo[2.2.1]hept-5-en-2-yloxy}carbonyl)amino]hexanoic acid |
| 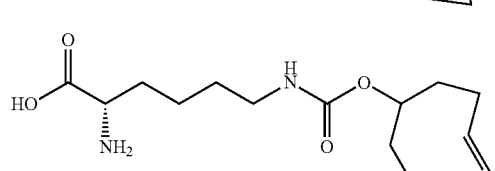 | (2S)-2-amino-6-({[(4E)-cyclooct-4-en-1-yloxy]carbonyl}amino)hexanoic acid |
| 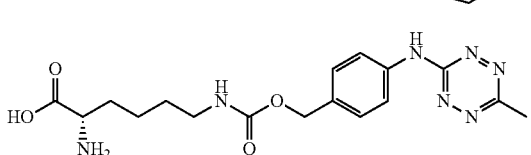 | (2S)-2-amino-6-{[({4-[(6-methyl-1,2,4,5-tetrazin-3-yl)amino]phenyl}methoxy)carbonyl]amino}hexanoic acid: |

Site Specific Conjugation of Proteins with Incorporated Non-Natural Amino Acids

Proteins having incorporated non-natural amino acids using methods according to the invention may be used for the preparation of functionalized protein conjugates. Molecules that may be conjugated to proteins having incorporated non-natural amino acids include (i) other proteins, e.g. antibodies especially monoclonal antibodies and (ii) PEG groups or other groups that may cause half life extension in the system. Moreover these modified proteins can be conjugated to drugs or nucleotides for targeted delivery of these potent compounds.

More details of certain embodiments are given below in the discussion of antibody drug conjugates.

Non-natural amino acids may conveniently contain a unique chemical group permitting conjugation in a targeted fashion without risk of side reaction with other amino acids. For example non-natural amino acids conveniently contain azide or alkyne groups permitting reaction with a molecule to be conjugated which contains a corresponding alkyne or azide group using the Huisgen 1,3-dipolar cycloaddition reaction.

A further aspect of the invention is a process for preparing a chemically modified target protein which comprises preparing a target protein according to the process according to an aspect of the invention and chemically modifying the resultant target protein.

Preferred conjugation chemistries of the invention include reactions which are orthogonal to the natural twenty amino acids. Such reactions do not interact or cause side reactions with the native 20 amino acids, they are specific to the functional groups associated with the reaction. Suitably the necessary functional groups are incorporated into the target protein via the nnAA.

Further, said reactions proceed under conditions which are not destructive to the protein, for instance aqueous conditions, with a pH range which is acceptable to the protein and maintains its solubility, at a temperature which does not lead to deleterious effects upon the protein.

Increasing the stability of the attachment moiety between the protein and the linker can be advantageous. Conventional methods conjugate to the thiol groups of cysteine by reaction with a maleimide forming a thiol ether. The thiol ether can undergo the reverse reaction releasing the linker drug derivative from the antibody. In an embodiment of the invention, the conjugation chemistry employed between an azide and an alkyne results in an aromatic triazole which is significantly more stable, and not as prone to reversibility.

In addition, the product of the reaction, the linkage between protein and payload, ought to be stable, equal to or greater than the stability associated with conventional linkages (amide, thiol ether). Though not an impediment to conjugation, it is often advantageous if the conjugation reactions can be done under native conditions, as this will eliminate an extra refolding processing step.

Preferred chemical conjugations for production of conjugates of the invention include: a 3+2 alkyne-azide cycloaddition; 3+2 dipolar cycloaddition; palladium based couplings including the Heck reaction; Sonogashira reaction; Suzuki reaction; Stille coupling; Hiyama/Denmark reaction; olefin metathesis; Diels-alder reaction; carbonyl condensation with hydrazine, hydrazide, alkoxy amine or hydroxyl amine; strain promoted cycloadditions, including Strain promoted azide alkyne cycloaddition; metal promoted azide alkyne cycloaddition; electron promoted cycloaddition; fragment extrusion cycloaddition; alkene cycloaddition followed by a b-elimination reaction.

According to one preferred embodiment, the incorporated amino acid contains an azide or an alkyne group and the process of chemical modification comprises reacting said azide or alkyne group with a reagent comprising an alkyne or azide group. The envisaged reaction is a Huisgen 1,3-dipolar cycloaddition reaction which leads to production of a triazole linkage. The reagent comprising an alkyne or azide group may be a protein (eg an antibody) or a toxin or a cytotoxic drug or a substance suitable for half life extension (eg a PEG group) which carries an alkyne or azide group optionally via a linker.

The alkyne group of use in said reaction is, for example, a terminal alkyne, a cyclooctyne such as a bicyclo[6.1.0] non-4-yne, dibenzocyclooctyne, and difluorocyclooctyne moiety.

In a variant reaction, the incorporated amino acid contains an azide or an alkene group and the process of chemical modification comprises reacting said azide or alkene group with a reagent comprising an alkene or azide group. The reagent comprising an alkene or azide group may be a protein (eg an antibody) or a toxin or a substance suitable for half life extension (eg a PEG group) which carries an alkyne or alkene group optionally via a linker.

When more than one nnAA is incorporated into a target protein (eg an antibody), the chemical modification may be the same or different. For example if two nnAAs are incorporated, one may be modified to be conjugated to a drug moiety and one may be modified to be conjugated to a PEG moiety.

In an embodiment, conjugation chemistry of the invention is used for preparing an antibody drug conjugate.

Target Proteins

Target proteins include antibodies.

Antibodies of the invention include full length antibodies and antibody fragments including Fab, Fab2, and single chain antibody fragments (scFvs) directed to TROP-2, SSTR3, B7S1/B7x, PSMA, STEAP2, PSCA, PDGF, RaSL, C35D3, EpCam, TMCC1, VEGF/R, Connexin-30, CA125 (Muc16), Semaphorin-5B, ENPP3, EPHB2, SLC45A3 (PCANAP), ABCC4 (MOAT-1), TSPAN1, PSGRD-GPCR, GD2, EGFR (Her1), TMEFF2, CD74, CD174 (IeY), Muc-1, CD340(Her2), Muc16, GPNMB, Cripto, EphA2, 5T4, Mesothelin, TAG-72, CA9 (IX), a-v-Integrin, FAP, Tim-1, NCAM/CD56, alpha folate receptor, CD44v6, Chondroitin sulfate proteoglycan, CD20, CA55.1, SLC44A4, RON, CD40, HM1.24, CS-1, Beta2 microglobulin, CD56, CD105, CD138, Lewis Y, GRNMP, Tomoregulin, CD33, FAP, CAIX, FasL Receptor, MMP matrix metallo proteases.

In a preferred embodiment of the invention, antibodies of the invention directed to tumor targets are conjugated to protein moieties selected from the following: immunostimulatory and proapoptotic proteins, particularly Immune stimulators such as IL-1alpha, IL-1beta, other IL-1 family members, any of the interleukins, including but not limited to IL-2, IL-4, IL-5, IL-6, IL-7, IL-12, IL-13, IL-15, IL-17 family, IL-18, IL-21, IL-22, IL-23, IL-28, or costimulatory ligands such as B7.1 and B7.2, TACI. Interferons such as any of the Type I IFN family (IFN alpha and beta and lambda) or the Type II IFN gamma. Hematopoietic growth factors such as GM-CSF. Chemokines including CXCL-1, CXCL-2, CXCL-5, CXCL-6, CXCL-8, CXCL-9, CXCL-10, and CXCL-11, CXCL-13, CCL-2, CCL-3, CCL-4, CCL-5, CCL-21, IP-10, Eotaxin, RANTES, PF4, GRO related peptides, IL-8. Proapoptotic ligands such as those of the TNF superfamily including FasL, TNF, PD-L1. Antimicrobial peptides such as alpha and beta defensins and cathelicidin LL37/hCAP18, histatins, cathepsin G, azurocidin, chymase, eosinophil derived neurotoxin, high mobility group 1 nuclear proteins, HMGB1, lactoferrin. ROS and RNS producing enzymes such as the members of NADPH oxidases (NOXs), nitric oxide synthase NOS, INOS), neutrophil granule proteins including proteases such as elastases and cathepsins, Azurocidin (also known as CAP37 or HBP), myeloperoxidase, perforin, granzymes.

In one embodiment the target protein is an anti-Her-2 antibody.

In one embodiment, the target protein is an anti-IL6 antibody.

In one embodiment, the target protein is an anti-PSMA antibody.

In a preferred embodiment, the anti-PSMA antibody is an scfv.

In a preferred embodiment, FGF21 is modified to contain non natural aminoacid lys-azide or propargyl lysine at position R131 and conjugated to a PEG moiety via a triazole linker.

PEG Moieties

Target proteins may be conjugated to PEG moieties. PEG moieties may be incorporated into antibody drug conjugates. The PEG moiety may typically have a molecular weight ranging between 5 kDa and 40 kDa. More preferably, the PEG moiety may have a molecular weight of around 20 kDa. PEG moieties may be straight chain or branched.

Antibody Drug Conjugates (ADCs)

Cell lines according to the invention are particularly useful for production of Antibody Drug Conjugates (recombinant antibody covalently bound by a synthetic linker to a given drug, typically a cytotoxic drug, or else a protein or a PEG group) which are homogeneous nature, in which the number of drugs (or other conjugated molecule) per antibody and position of those drugs upon the antibody are explicitly controlled, whereby monoclonal antibodies containing incorporated non-natural amino acids are obtained and site specifically conjugated to a linker carrying a drug moiety (or other conjugated molecule) through orthogonal chemistry.

Suitably, the present invention provides a process to obtain ADCs including the following steps:

1. Introducing into a stable cell line of the invention one or more plasmids carrying the DNA sequence coding for a full length antibody, whereby a stop codon is introduced at specific positions within the sequence
2. Purify the modified antibody with non natural amino acid (nnAA) installed at desired position(s).
3. React a cytotoxin-linker derivative modified to include a functional group complimentary to the nnAA installed in the antibody with the modified antibody containing a complementary reactive group through an orthogonal chemistry
4. Purify the resulting ADC Thus, the present invention also provides ADCs whereby the antibody component has been modified to incorporate non natural aminoacids bearing a unique reactive functional group at desired positions, whereby such functional group allows conjugation to a drug moiety (or protein or PEG group).

In an embodiment the present invention provides an antibody conjugate comprising an anti-Her-2 antibody which is conjugated to one or more moieties (e.g. one, two, three or four, preferably one or two, especially one) selected from protein, drug and PEG moieties via linkers comprising a triazole moiety.

In particular, the triazole moiety may be formed by reaction of an azide or alkyne moiety in the side chain of a non-natural amino acid incorporated into the sequence of the anti-Her-2 antibody and an alkyne or azide moiety attached to the protein, drug or PEG moiety.

In one embodiment, the triazole moiety is formed by reaction of an azide or alkyne moiety in the side chain of a non-natural amino acid incorporated into the sequence of the anti-Her-2 antibody and an alkyne or azide moiety attached to the protein, drug or PEG moiety under conditions of Cu(I) catalysis.

In another embodiment, an antibody conjugate comprises an antibody which is conjugated to one or more moieties selected from drug and PEG moieties via linkers comprising a triazole moiety in which the triazole moiety is formed by reaction of an azide moiety in the side chain of a non-natural amino acid incorporated into the sequence of the antibody and an alkyne moiety attached to the drug or PEG moiety and in which the alkyne moiety is a cyclooctyne moiety.

In another embodiment, an antibody conjugate comprises an antibody which is conjugated to one or more moieties selected from drug and PEG moieties via linkers comprising a triazole moiety in which the triazole moiety is formed by reaction of an alkyne moiety in the side chain of a non-natural amino acid incorporated into the sequence of the antibody and an azide moiety attached to the drug or PEG moiety and in which the alkyne moiety is a terminal alkyne, a substituted alkyne or a cyclooctyne moiety.

The cyclooctyne moiety may, for example, be a bicyclo [6.1.0]non-4-yne, dibenzocyclooctyne, and difluorocyclooctyne moiety.

The non-natural amino acid incorporated into the sequence of the antibody is suitably a non-natural amino acid substrate for PylRS, particularly a non natural lysine analog such as (S)-2-amino-6((2-azidoethoxy)carbonylamino)hexanoic acid.

Antibodies

In the present invention ADCs include the use of full length antibodies as well as antibody fragments such as, but not limited to Fab, Fab2, and single chain antibody fragments.

Antibodies suitable for conjugation to cytotoxins include those targeted against: anti-Her2, anti-IL-6, TROP-2, SSTR3, B7S1/B7x, PSMA, STEAP2, PSCA, PDGF, RaSL, C35D3, EpCam, TMCC1, VEGF/R, Connexin-30, CA125 (Muc16), Semaphorin-5B, ENPP3, EPHB2, SLC45A3 (PCANAP), ABCC4 (MOAT-1), TSPAN1, PSGRD-GPCR, GD2, EGFR (Her1), TMEFF2, CD74, CD174 (IeY), Muc-1, CD340(Her2), Muc16, GPNMB, Cripto, EphA2, 5T4, Mesothelin, TAG-72, CA9 (IX), a-v-Integrin, FAP, Tim-1, NCAM/CD56, alpha folate receptor, CD44v6, Chondroitin sulfate proteoglycan, CD20, CA55.1, SLC44A4, RON, CD40, HM1.24, CS-1, Beta2 microglobulin, CD56, CD105, CD138, Lewis Y, GRNMP, Tomoregulin, CD33, FAP, CAIX, FasL Receptor, MMP matrix metallo proteases.

One particular antibody of interest is an anti-Her-2 antibody.

Another particular antibody of interest is an anti-PSMA antibody, especially a scfv.

Said scfv may, for example, be conjugated to an auristatin, paclitaxel, doxorubicin, or amanitin derivative.

EXAMPLES OF THE INVENTION

Example 1

Generation of Intragenic Promoter Elements

Site directed mutagenesis was utilized to generate the following mutations in the tRNApyl gene: A at position 52 (referred to the WT *Methanosarcina mazei* tRNApyl sequence, SEQ ID No 3)) was mutated into C; A at position 10 was mutated into G and T at position 14 was mutated into A.

Figure 4:
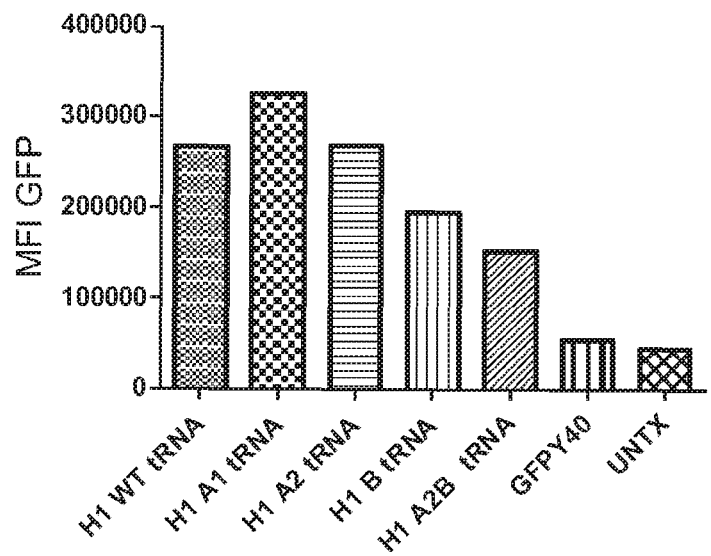
FIG. 4. tRNA mutants retain function when expressed by the H1 promoter, as demonstrated by amber suppression-dependent GFP expression FIG. 5. Functional tRNA expression shown from use of mutant tRNApyl comprising an intragenic polIII promoter, demonstrated by increased amber suppression-dependent GFP expression FIG. 6. tRNA mutants are functional and retain orthogonality in mammalian cells FIG. 7. Increasing gene dose by increasing the number of genes in the same construct, results in increased amber suppression-dependent GFP expression FIG. 8. type 4 5' promoter elements allow expression of a tRNA containing a functional B-box, as determined by amber suppression-dependent GFP expression FIG. 9. type 4 5' promoter elements and the tRNA B mutant alone enable higher levels of tRNA function than the wild type tRNA.
Figure 5:
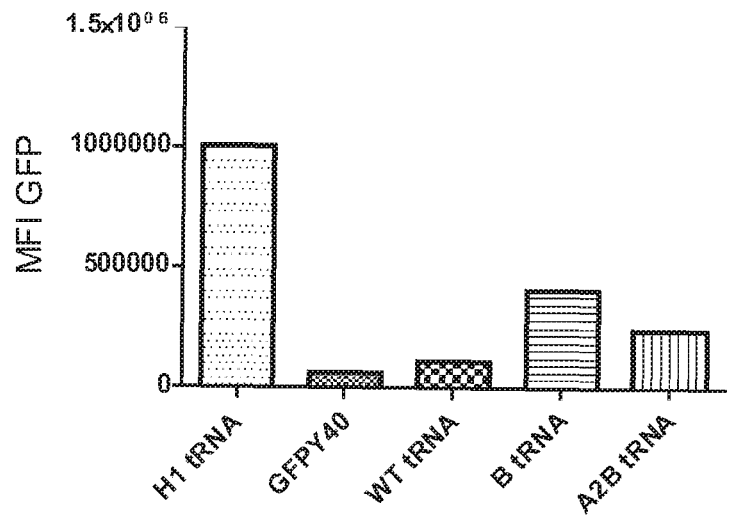

In particular, constructs containing a single mutation A52C (Construct named tRNA-B, SEQ ID No 9), all the mutations described above, namely A52C, A10G and T14A (tRNA-A2B, SEQ ID No 10) or mutations in the A box alone (A10G and T14A, tRNA-A2, SEQ ID No 11 or A10G, tRNA-A1, SEQ ID No 7) were made Demonstration of Functional Expression of tRNApyl with Intragenic Promoter To assess the function of the tRNA variants, an in vitro assay was established where cells are transiently transfected with a tRNA construct and a reporter construct encoding GFP containing an amber codon interrupting its reading frame (GFPY40). HEK293 cells stably expressing pylRS were transiently transfected with various tRNA constructs (1 ug) and the GFPY40 reporter (1 ug). In the absence of elements that support amber suppression, a truncated GFP protein is generated and the cell is not fluorescent. However, the introduction of a functional tRNA and the presence of a nnAA that supports amber suppression allows for the production of full length GFP resulting in fluorescent cells. The level of GFP expression reflects the efficiency of amber suppression and is quantified by flow cytometry. tRNA genes encoding wild type tRNApyl (WT tRNA), or containing mutations in the B-box (B tRNA—SEQ ID No 9), in both the A and B box (A2B tRNA—SEQ ID No 10), or in the A box (A1 tRNA-SEQ ID No 7; or A2 tRNA SEQ ID No 11), all under control of the H1 promoter were generated by site directed mutagenesis and assayed. The H1 promoter ensured that the variants were expressed and allowed us to examine the functional effects of the mutations introduced into the tRNA genes. In addition a sample transfected with GFPY40 alone was generated to establish background GFP levels. The transfected cells were grown in presence of the aminoacid analogue lys azide (2 mM) and incubated for 18 hours. GFP fluorescence was then assayed by flow cytometry and mean fluorescence intensity determined for each sample. Data were analysed with FCS Express and the mean fluorescence intensity of each sample determined using markers that constrain the data set to cells showing fluorescence above negative controls. The data, as shown in FIG. 4, demonstrates that the incorporation of mutations at the A-box site (H1-A1 tRNA and H1 A2 tRNA) does not affect the activity of the tRNA with respect to its capacity to support amber suppression relative to the wild type H1 WT tRNA. The constructs encoding B tRNA and A2B tRNA support amber suppression, albeit at a lower level than the WT tRNA. The constructs thus are functional and may contain the necessary genetic sequence to enable the expression of the tRNA also in the absence of an upstream promoter element such as the H1 promoter.

To begin to assess whether the tRNA mutations can support expression of the tRNA we assayed tRNA constructs encoding the wild type tRNA in the absence of the H1 promoter. Constructs encoding wild type tRNApyl (WT tRNA) or containing mutations in the B-box (B tRNA—SEQ ID No 9) or in both the A and B box (A2B; A2B tRNA—SEQ ID No 10) were assayed using our in vitro amber suppression assay described above. WT tRNA under control of the H1 promoter (H1-tRNA) was used as a positive control, and in addition one sample was transfected only with the GFPY40 reporter to illustrate background amber suppression in the absence of tRNA. The transfected cells were exposed to 2 mM lys-azide nnAA and cells incubated for three days. GFP expression was examined by flow cytometry and mean fluorescence intensity determined. These data were plotted and shown in the FIG. 5. The H1-tRNA construct had been shown previously to enable efficient amber suppression (MFI=1,004,228.00). However, no GFP fluorescence was observed in a sample lacking tRNA (GFPY40; MFI=65,929) and low levels in samples containing wt tRNA (MFI=114,478.1). tRNA mutants B tRNA (MFI=410,131.1) and A2B tRNA (MFI=242,747.9) enabled four-fold and 2.5 fold higher expression of GFP respectively than the wt tRNA construct. This data shows that the B and A2B mutations reconstitute a functional intragenic promoter and that the expressed tRNA is functional as it can mediate the delivery of nnAA to the target protein.

Figure 6:
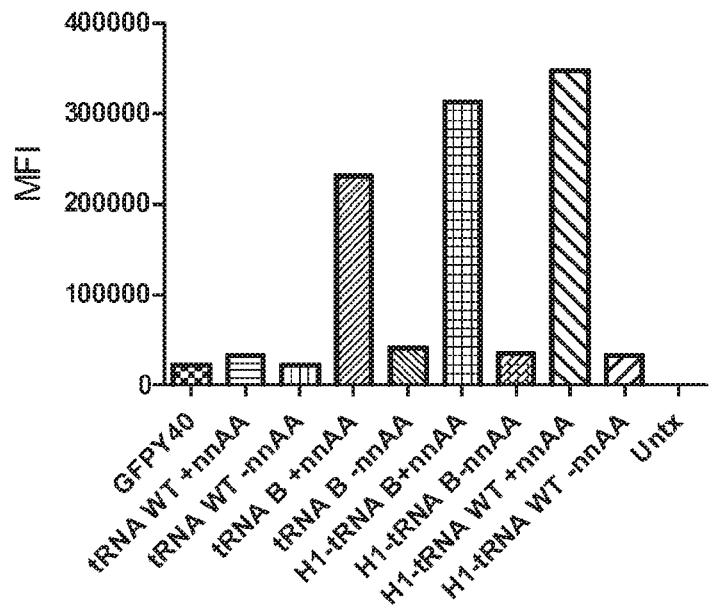

Having established that the B mutation introduced into the pyltRNA sequence enabled expression of the tRNA that supported amber suppression we then asked whether this mutation affected the orthogonality of the tRNA and led to the incorporation of natural amino acids. To do this 3H7 cells were transiently transfected with expression constructs encoding WT-tRNA, B-tRNA, H1-tRNA and H1-B tRNA along with the GFPY40 reporter. Transfected cells were grown in the presence of 2 mM lys azide or absence of nnAA as indicated (FIG. 6), and GFP expression assessed by flow cytometry after three days. In addition, a sample transfected only with GFPY40 was examined to determine background amber suppression levels in the absence of tRNA. FIG. 6 shows that in the presence of lys-azide H1-tRNA (MFI=347, 958), H1-B tRNA (MFI=313,386) and B-tRNA (MFI=232, 505) all support robust amber suppression and expression of full length GFP above background levels (MFI=23,487). In the absence of nnAA background levels of GFP expression were observed in cells containing these three constructs (MFI=33,452; 36,217; 42,104 respectively). These data show that B tRNA is orthogonal and does not promote amber suppression levels above background in the absence of nnAA including a construct previously shown to support high levels of expression (H1-tRNA B). A comparison of GFP expression between the WT tRNA (MFI 33,781) and tRNA B (232,505) lacking extragenic promoter elements confirms that the B mutation generates a functional intragenic promoter. Indeed, the B tRNA construct enabled a seven-fold increase in the level of amber suppression dependent expression of GFP over WT tRNA.

Example 2

Copy Number and Amber Suppression

In an effort to increase the efficacy of amber suppression by the tRNA-B construct, we assessed whether increased copy numbers led to an increased activity.

Two copies of the WT, B, or A2B tRNA were cloned in tandem to generate a single vector containing two copies of WT, B, or A2B tRNA. To assess the effect of increased gene doses by these constructs, cells expressing WTpylRS were transiently transfected with the tRNA constructs and the GFPY40 reporter construct and GFP expression assayed after two days. The data in FIG. 7 show that B (MFI=67,489) and A2B tRNA (MFI=61,950) can support amber suppression levels above those by WT tRNA (MFI=18,002) confirming the observation that the B and A2B tRNAs contain functional promoter elements. Furthermore, we observed that tandem copies of B (MFI=110,941) and A2B tRNA (MFI=96,158) led to a concomitant increase in the efficacy of amber suppression as determined by GFP expression. Gene dose did not improve WT tRNA amber readthrough (MFI=20,617).

Example 3

Expression of tRNApyl Under Extragenic Promoters and Hybrid (Type 4) Promoters

The H1 promoter has been shown here and by others to support expression of tRNApyl. However, significant deleterious effects have been observed by the use of polIII/Type3 (e.g. H1 and U6) promoters in mammalian cells. Thus, to overcome these deficiencies, a set of extragenic promoters elements, known to govern RNA expression, were assessed for their capacity to express tRNApyl. Extragenic promoter elements are known to regulate the expression of human Vault, EBER and 7SL RNA (Englert et al., 2004; Kickhoefer et al., 2003; Howe & Shu 1989). Each of these promoters has been shown to recruit the transcription factor TFIIIc, and not SNAPc (used by U6 and H1) (Moqtaderi et al., 2010) (Felton-Edkins et al (2006) J Biol Chem 281:33871). Interestingly, efficient transcription by these promoters requires both intragenic and extragenic regulatory sequences (Englert et al., 2004; Kickhoefer et al., (2003); and Howe & Shu (1989)). The identification of a functional tRNApyl containing consensus A and B-boxes opened the door to their use in the expression of the tRNApyl. The promoter elements know to regulate Vault, 7SL, and EBER2 RNA were constructed from previously described sequences (Englert et al., 2004; Kickhoefer et al., 2003; Howe & Shu 1989). We tested the promoters for human Vault and 7SL RNA genes and Epstein Barr virus EBER gene as extragenic promoter elements by placing them 5' of genes encoding WT tRNA, B tRNA, A2B tRNA, and additional variants containing A10G and A52C (AB tRNA; SEQ ID No. 8) or containing a single mutation at A10G (A1 tRNA; SEQ ID No. 7).

The activity of each construct was assessed by transient transfection into cells stably expressing WT pylRS with the GFPY40 reporter as described above. For this experiment, 1 ug of a PCR product encoding each of the indicated constructs was used. In each case, cells were exposed to the lys azide nnAA for three days and GFP levels assayed by flow cytometry. Mean fluorescence intensities were determined for each sample and plotted (FIG. 8). A sample transfected only with GFPY40 (no tRNA) was used to establish background amber suppression in the absence of tRNA (no tRNA, MFI=137,589). In addition, a sample transfected with H1-WT tRNA was to define high expression levels of GFP and function of the tRNA (H1 WT tRNA, MFI=828,503) and low levels of amber suppression determined by tRNA lacking intragenic promoters (WT tRNA, MFI=117,626). As shown in FIG. 8, the use of extragenic promoters (EBER, Vault and 7SL) showed improved expression levels of the GFP reporter over WT tRNA with EBER, Vault and 7SL promoters. However, improved performance from each of these promoters required intragenic tRNA elements. Indeed, cells transfected with 7SL WT tRNA showed minimal amber suppression (7SL WT tRNA, MFI=106,075). However, relative amber suppression efficacy improved with tRNA containing conserved A and B-box elements (7SL tRNA A1, MFI=114,393; 7SL AB, MFI=210,380; 7SL A2B, MFI=245,120). Interestingly, the highest amber suppression levels was observed with the tRNA constructs containing only a functional B-box (7SL B tRNA, MFI=265,396). This general trend was also observed with the Vault RNA promoter. Constructs containing a functional B box (Vault B tRNA, MFI=170,838) showed improved performance over those containing both consensus A and B boxes (Vault A2B tRNA, MFI=154,445) and constructs of the wild type tRNA (Vault WT tRNA, MFI=102,415). The EBER promoter functioned best when the tRNA contained conserved A and B-box elements (EBER A2B tRNA, MFI=136,196). This construct outperformed tRNA containing a B mutation (EBER B tRNA, MFI=113,496) and tRNA containing a single B-box and a partially reconstituted A box (EBER AB tRNA, MFI=119,719), and unmodified tRNA (EBER WT tRNA, MFI=99,393). Our data show that the extragenic RNA promoters for Vault snRNA, 7SL RNA and EBER RNA can support expression and function of tRNApyl. The efficacy of amber suppression is dependent on the presence of a functional B-box.

Figure 9:
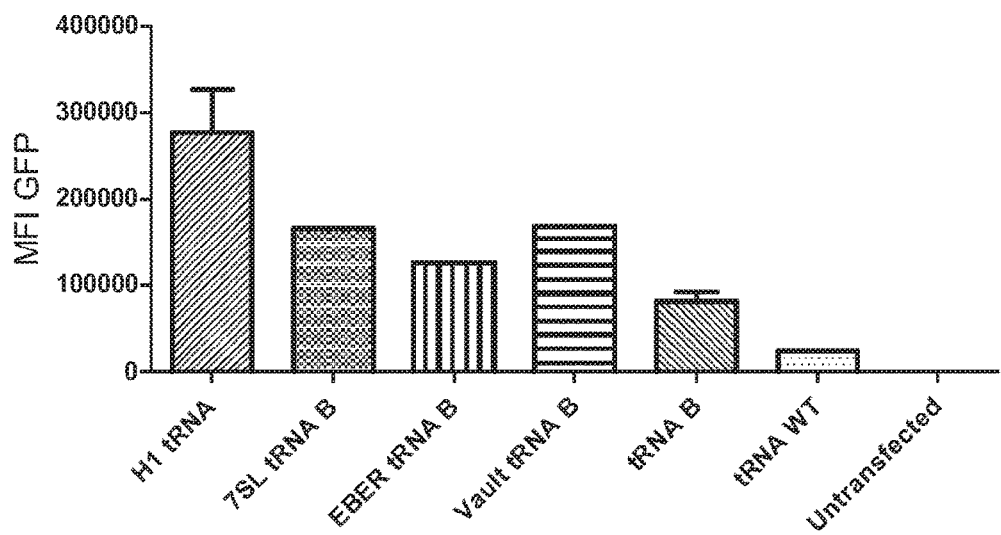

We then tested amber suppression activity to directly compare the levels of tRNA dependent amber suppression between the various functional tRNA expression constructs (FIG. 9). In this assay, cells stably expressing WTpylRS were transiently transfected with 1 ug of GFPY40 reporter and 1 ug of one of the tRNA expression plasmids (H1-tRNA, Vault B tRNA, 7SL B tRNA, EBER B tRNA, B tRNA or WT tRNA). FIG. 9 shows that both 7SL-B tRNA (MFI=167,024) and Vault-B tRNA (MFI=168,298) can support amber suppression activity comparable to that seen with the H1-tRNA (MFI=241,901) construct, resulting in an improvement of activity compared to the tRNA-B construct (MFI=89,869) and WT tRNA (MFI=25,459), relative to H1-tRNA (FIG. 8).

Figure 10:
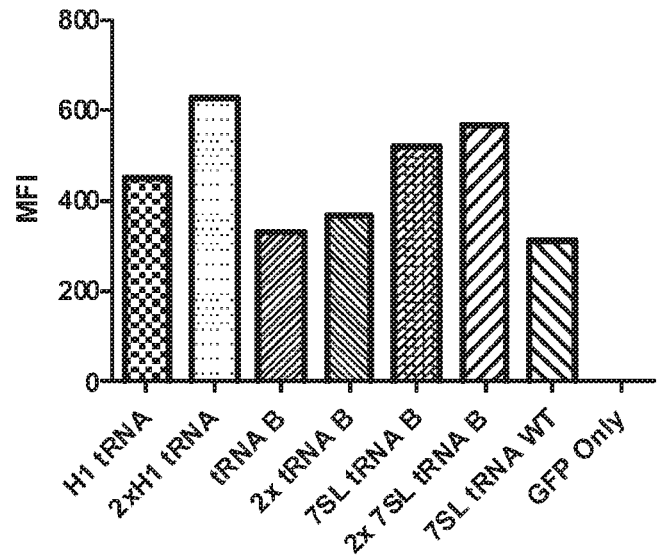
FIG. 10. Increasing gene dose by increasing the number of genes in the same construct, results in increased amber suppression-dependent GFP expression FIG. 11. tRNApyl expression driven by upstream tRNAglu and tRNAasp genes.

In an effort to increase the amber suppression levels that are supported by the extragenic 7SL promoter with B tRNA we examined the effects of tandem repeats of 7SL-tRNA-B relative to H1 tRNA. To do this, two copies of the 7SL-tRNA-B constructs were cloned into a single vector and amber suppression levels assessed using transient transfections of cells stably expressing the WTpylRS along with GFPY40. Cells were incubated with lys azide for three days and GFP levels quantified by flow cytometry. FIG. 10 shows that increased gene copies of 7SL-B tRNA as well as H1-tRNA results in improved amber suppression efficacy and GFP expression levels. In this experiment cell transfected with GFP only were used as a negative control (MFI=0). Cells transfected with a tandem copy of the H1-tRNA (2×H1 tRNA, MFI=629) resulted in a 28% increase in expression of the GFPY40 reporter construct over a single copy of the H1 tRNA (MFI=453). The same effect was observed with tandem repeats of tRNA lacking an external promoter but containing a functional B box. Here tandem repeats of tRNA B (2×tRNA B, MFI 366) showed a 10% improvement over the single gene copy (tRNA B, MFI=329). Tandem copies of the 7SL tRNA B (2×7SL tRNA B, MFI=568), also showed a 8.5% improvement over the signal observed with a single gene (7SL tRNA B, MFI=520). A construct encoding wild type tRNA lacking a functional B box under control of the 7SL promoter has been previously shown to be less effective than 7SL tRNA B. This former construct was included in this analysis to verify this effect (7SL tRNA WT, MFI=312). Indeed this data confirms previous experiments that the B mutation improves the performance of the 7SL-tRNA construct. These data show that increased gene numbers can improve the efficacy of the suppressor tRNA. Furthermore these data also show that the 7SL promoter is equivalent to the H1 promoter in facilitating the expression of tRNApyl.

Example 4

Expression of tRNApyl as Part of a Bicistronic Message

We also tested the utility of a bicistronic tRNA expression construct for its ability to express tRNApyl. Here, the murine tRNA Glu and tRNA Asp were utilized. In each case, multiple repeats of the constructs were generated to increase activity (3×Glu-pyl and 2×Asp-pyl). Here, 3H7 cells were transiently transfected with 1 ug of the reporter construct GFPY40 and 1 ug of the indicated tRNA expression vectors (FIG. 11) and incubated with lys-azide for three days. Data were collected by flow cytometry and mean fluorescence intensities for each sample were plotted. We observed that the bicistronic constructs enabled high levels of amber suppression relative to the H1-tRNA positive control. tRNA expression cassettes consisting of three tandem repeats of the murine tRNA glu and pyltRNA pair (3×Glu, MFI=419) and two tandem repeats of the murine tRNA asp-pyl tRNA pair (2×Asp, MFI=419) showed >90% of the signal generated by H1-tRNA (MFI=453) Indicating their ability to efficiently produce functional tRNA. In addition, 7SL tRNA B (MFI=520) also demonstrated efficient expression of the tRNA. The construct consisting of the 7SL WT tRNA (MFI=312) was included as a metric for low efficiency. In addition cell lines containing only the GFPY40 reporter were used as negative controls (MFI=0). This data indicates that the bicistronic construct is an efficient method for the expression of tRNAs lacking functional A and B-box elements and furthermore demonstrates that mammalian cells can process these RNA molecules to generate mature and functional tRNAs.

REFERENCES

1. Blight et al. 2004 Nature. 431 333-335.
2. Buvoli et al. 2000 Mol Cell Biol. 3116-3124.

3. Chen, P., 2009 Agnew Chem Int Ed Engl. 48, 4052-55.
4. Ehlert, et al., 2010 BMC Neuroscience, 11(20), p. 1471
5. Englert et al., 2004 Biochimie 86 (2004) 867-874
6. Felton-Edkins et al (2006) J Biol Chem 281:33871
7. Francis M A et al., 1990 Mol Cell Biol 10(9):4486-94.
8. Giering, et al., 2008 Mol Ther. 16(9):1630-6
9. Hancock et al. JACS 2010, 132, 14819-24
10. Hecht et al., 1978 JBC 253, 4517-20.
11. Herold et al., 2008 PNAS 105, 18507-12.
12. Howe J G et al., 1989 Cell. 57(5):825-34.
13. Hudziak R M, et al., 1982 Cell 31(1):137-46.
14. Kavran et al., 2007 PNAS 104, 11268-73.
15. Kohrer et al., 2001 PNAS 98, 14310-15;
16. Kohrer et al., Chem & Biol., (2003) 10, 1095-1102;
17. Laski F A et al., 1982 Proc Natl Acad Sci USA.; 79(19):5813-7.
18. Liebman S W. and Sherman, F. 1976 Genetics, 82, 233-249.
19. Liebman, S W et al., 1976 Genetics 82, 251-272.
20. Liu W. et al. 2007, Nature methods, 4; 239-244.
21. Mossink et al., 2002 294(1-2):225-32
22. Mukai et al 2008 BBRC 371, 818-823
23. Naykova et al. 2003 J Mol. Evol. 57:520-532.
24. Neumann et al. 2008 Nat. Chem. Biol. 4, 232-234.
25. Nguyen et al., 2009 *J. Am. Chem. Soc.* 131 (25), pp 8720-8721
26. Nozawa 2009, Nature. 457 1163-67.
27. Paul et al., 2003 Mol. Ther., 7(2), pp. 237-247
28. Pettit et al., 1997 Fortschr. Chem. Org. Naturst 70, 1-79
29. Sakamoto, K. 2002 Nucl. Acid Res. 30, 4692-4699.
30. Schmidt 0 et al., 1980 Nature 287(5784):750-2.
31. Shan L. et al., J Gene Med. (2006) 8, 1400-1406.
32. Senter P. et al., 2003 Blood 102, 1458-65.
33. Stegmeier, et al., 2005 PNAS, 102(37), p. 13212-13217.
34. Straby K B, 1988 Nucleic Acids Res. 16(7):2841-57.
35. Takimoto j. 2009, Mol. Biosystems, 5, 931-34.
36. Wang w. Nature Neuro. 2007, 8; 1063-1072.
37. Ye, S. 2008, JBC 283, 1525-1533.
38. Yanagisawa 2008 Chem & Biol. 15, 1187-1197.
39. Wang et A1, 2011 Aijun Wang, Natalie Winblade Nairn, Marcello Marelli and KennethGrabstein (2012). Protein Engineering with Non-Natural Amino Acids, Protein Engineering, Prof. Pravin Kaumaya (Ed.), ISBN: 978-953-51-0037-9, InTech, Available from: www.intechopen.com.
40. Dieci, G., Conti, A., Pagano, A. & Carnevali, D., 2013. Identification of RNA Polymerase III-transcribed genes in eukaryotic genomes. *Biochim. Biophys. Acta*, Volume 1829, pp. 296-305.
41. Ehlert, E., Eggers, R., Niclou, S. & Verhaagen, J., 2010. Cellular toxicity following application of adenoassociated viral vector-mediated RNA interference in the nervous system. *BMC Neuroscience,* 11(20), p. 1471.
42. Giering, J., Grimm, D., Storm, T. & Kay, M., 2008. Expression of shRNA from a tissue-specific pol II promoter is an effective and safe RNAi therapeutic. *Mol. Ther.*, Volume 144, pp. 1630-6.
43. Hancock, S. M., Uprety, R., Deiters, A. & Chin, J. W., 2010. Expanding the genetic code of yeast for incorporation of diverse unnatural amino acids via a pyrrolysyl-tRNA synthetase/tRNA pair. *JACS*, Volume 132, pp. 14819-24.
44. Paul, C. et al., 2003. Localized Expression of Small RNA Inhibitors. *Mol. Ther.,* 7(2), pp. 237-247.
45. Stegmeier, F. et al., 2005. A lentiviral microRNA-based system for single-copy polymerase II-regulated RNA interference in mammalian cells. *PNAS,* 102(37), p. 13212-13217.
46. Wang, Q. & Wang, L., 2012. Genetic incorporation of unnatural amino acids into proteins in yeast. *Methods Mol. Biol.*, Volume 794, pp. 199-213.
47. Englert, M., Martha, F., Junker, V. & Beier, H., 2004. Novel upstream intragenic control elements for the RNA polymerase III-dependent transcription of human 7SL RNA genes. Biochimie, Volume 86, pp. 867-874.
48. Howe, J. & Shu, M.-D., 1989. Epstein Barr virus small RNA (EBER) Genes: unique transcription units that combine RNA polymerase II and III promoter elements. Cell, Volume 57, pp. 825-834.
49. Kickhoefer, V. et al., 2003. Identification of conserved vault RNA expression elements and a non expressed mouse vault RNA gene. Gene, Volume 309, pp. 65-70.
50. Moqtaderi, Z. et al., 2010. Genomic binding profiles of functionally distinct RNA polymerase Ill transcription complexes in human cells. Nature Struct. & Mol. Biol., 17(5), pp. 635-641.

Sequence Listing
Underlined sequences identify A box and/or B box sequences
Bold characters identify mutated nucleotides

```
                                                      SEQ ID No 1
>tRNApyl Methanosarcina_barkeri, WT; coding sequence
GGAAACCTGATCATGTAGATCGTGGACTTCTAAATCCGCAGCCGGGTAGATTCCCGGGGTTTCCG SEQ ID No 2
>tRNApyl Methanosarcina acetivorans, WT; coding sequence
GGAAACCTGATCATGTAGATCGAATGGACTCTAAATCCGTTCAGCCGGGTTAGATTCCCGGGGTTTCCG SEQ ID No 3
>tRNApyl Methanosarcina mazei Gol, WT; coding sequence
GGAAACCTGATCATGTAGATCGAATGGACTCTAAATCCGTTCAGCCGGGTTAGATTCCCGGGGTTTCCG SEQ ID No 4
>tRNApyl Methanococcoides burtonii DSM, WT; coding sequence
GGAGACTTGATCATGTAGATCGAACGGACTCTAAATCCTTTCAGCCGGGTTAGATTCCCGGAGTTTCCG SEQ ID No 5
>tRNApyl Desulfobacterium hafniense, WT; coding sequence
GGAAACCTGATCATGTAGATCGTGGACTCTAAATCCGCAGCCGGGTAGATTCCCGGGGTTTCCG SEQ ID No 6
>Terminator sequence used for WT and mutant A-box and/or B-box
tRNApyl constructs
gacaagtgcggttttttt
```

-continued

SEQ ID No 7
> tRNApyl Methanosarcina mazei A10G mutation ("tRNA-A1"); coding
sequence
ggaaacctggtcatgtagatcgaatggactctaaatccgttcagccgggttagattcccggggtttccg SEQ ID No 8
tRNApyl Methanosarcina mazei A10G A52C mutation ("tRNA-AB"); coding
sequence
ggaaacctggtcatgtagatcgaatggactctaaatccgttcagccgggttcgattcccggggtttccg SEQ ID No 9
tRNApyl Methanosarcina mazei A52C mutation ("tRNA-B"); coding sequence
ggaaacctgatcatgtagatcgaatggactctaaatccgttcagccgggttcgattcccggggtttccg SEQ ID No 10
tRNApyl Methanosarcina mazei A10G, T14A, A52C mutations ("tRNA-A2B");
coding sequence
ggaaacctggtcaagtagatcgaatggactctaaatccgttcagccgggttcgattcccggggtttccg SEQ ID No 11
tRNApyl Methanosarcina mazei A52C, T14A, mutations ("tRNA-A2"); coding
sequence
ggaaacctgatcaagtagatcgaatggactctaaatccgttcagccgggttcgattcccggggtttccg SEQ ID No 12
7SL Promoter 5'region sequence
cccagttgatgacgtcaccataccacagcttctagtgctattctgcgccggtatccgacc SEQ ID No 13
Spacer used in 7SL constructs
acca SEQ ID No 14
7SL tRNA-WT construct
cccagttgatgacgtcaccataccacagcttctagtgctattctgcgccggtatccgaccaccaggaaac ctgatcatgtagatcgaatggactctaaatccgttcagccgggttagattcccggggtttccggacaagt gcggttttt SEQ ID No 15
7SL tRNA-B construct
cccagttgatgacgtcaccataccacagcttctagtgctattctgcgccggtatccgaccaccaggaaac ctgatcatgtagatcgaatggactctaaatccgttcagccgggttcgattcccggggtttccggacaagt gcggttttt SEQ ID No 16
7SL tRNA-A1 construct
cccagttgatgacgtcaccataccacagcttctagtgctattctgcgccggtatccgaccaccaggaaac ctggtcatgtagatcgaatggactctaaatccgttcagccgggttagattcccggggtttccggacaagt gcggttttt SEQ ID No 17
7SL tRNA-AB construct
cccagttgatgacgtcaccataccacagcttctagtgctattctgcgccggtatccgaccaccaggaaac ctggtcatgtagatcgaatggactctaaatccgttcagccgggttcgattcccggggtttccggacaagt gcggttttt SEQ ID No 18
7SL tRNA-A2B construct
Cccagttgatgacgtcaccataccacagcttctagtgctattctgcgccggtatccgaccaccaggaaac ctggtcaagtagatcgaatggactctaaatccgttcagccgggttcgattcccggggtttccggacaagt gcggttttt SEQ ID No 19
Terminator sequence used in the 7SL, Vault, EBER constructs
GACAAGTGCGGTTTTT -continued SEQ ID No 20
Vault Promoter 5'region sequence
tggtcgctgagtcatgctgaagcactctcttttttgactcactctttgtgacgtaggtctttctcaccagt caataaaatataatccgaaagcaacctc SEQ ID No 21
Spacer used for Vault-tRNA constructs
CCACCA SEQ ID No 22
Vault tRNA-WT construct
tggtcgctgagtcatgctgaagcactctcttttttgactcactctttgtgacgtaggtctttctcaccagt caataaaatataatccgaaagcaacctcccaccaggaaacctgatcatgtagatcgaatggactctaaat ccgttcagccgggttagattcccggggtttccggacaagtgcggttttt SEQ ID No 23
Vault tRNA-B construct
tggtcgctgagtcatgctgaagcactctcttttttgactcactctttgtgacgtaggtctttctcaccagt caataaaatataatccgaaagcaacctcccaccaggaaacctgatcatgtagatcgaatggactctaaat ccgttcagccgggttcgattcccggggtttccggacaagtgcggttttt SEQ ID No 24
Vault tRNA-AB construct
tggtcgctgagtcatgctgaagcactctcttttttgactcactctttgtgacgtaggtctttctcaccagt caataaaatataatccgaaagcaacctcccaccaggaaacctggtcatgtagatcgaatggactctaaat ccgttcagccgggttcgattcccggggtttccggacaagtgcggttttt SEQ ID No 25
Vault tRNA-A2B construct
Tggtcgctgagtcatgctgaagcactctcttttttgactcactctttgtgacgtaggtctttctcaccagt caataaaatataatccgaaagcaacctcccaccaggaaacctggtcaagtagatcgaatggactctaaat ccgttcagccgggttcgattcccggggtttccggacaagtgcggttttt SEQ ID No 26
EBER2 Promoter 5'region sequence
agatgcacgcttaaccccgcctacaaccgtgacgtagctgtttaccagcatgtatagagttacggttcgc tacatcaaac SEQ ID No 27
Spacer used in EBER constructs
acca SEQ ID No 28
EBER2 tRNA-WT construct
agatgcacgcttaaccccgcctacaaccgtgacgtagctgtttaccagcatgtatagagttacggttcgc tacatcaaacaccaggaaacctgatcatgtagatcgaatggactctaaatccgttcagccgggttagatt cccggggtttccggacaagtgcggttttt SEQ ID No 29
EBER2 tRNA-B construct
agatgcacgcttaaccccgcctacaaccgtgacgtagctgtttaccagcatgtatagagttacggttcgc tacatcaaacaccaggaaacctgatcatgtagatcgaatggactctaaatccgttcagccgggttcgatt cccggggtttccggacaagtgcggttttt SEQ ID No 30
EBER2 tRNA-A1 construct
agatgcacgcttaaccccgcctacaaccgtgacgtagctgtttaccagcatgtatagagttacggttcgc tacatcaaacaccaggaaacctggtcatgtagatcgaatggactctaaatccgttcagccgggttagatt cccggggtttccggacaagtgcggttttt

```
                                                              SEQ ID No 31
EBER2 tRNA-AB construct
agatgcacgcttaaccccgcctacaaccgtgacgtagctgtttaccagcatgtatagagttacggttcgc tacatcaaacaccaggaaacctggtcatgtagatcgaatggactctaaatccgttcagccgggttcgatt cccggggtttccgggacaagtgcggttttt SEQ ID No 32
EBER2 tRNA-A2B construct
agatgcacgcttaaccccgcctacaaccgtgacgtagctgtttaccagcatgtatagagttacggttcgc tacatcaaacaccaggaaacctggtcaagtagatcgaatggactctaaatccgttcagccgggttcgatt cccggggtttccgggacaagtgcggttttt SEQ ID No 33
H1 promoter sequence
Aatatttgcatgtcgctatgtgttctgggaaatcaccataaacgtgaaatccctatcagtgatagagact tataagttccctatcagtgatagagacacca SEQ ID No 34
H1 tRNA-WT construct
aatatttgcatgtcgctatgtgttctgggaaatcaccataaacgtgaaatccctatcagtgatagagact tataagttccctatcagtgatagagacaccaggaaacctgatcatgtagatcgaatggactctaaatccg ttcagccgggttagattcccggggtttccggacaagtgcggtttttt SEQ ID No 35
H1 tRNA-B construct
Aatatttgcatgtcgctatgtgttctgggaaatcaccataaacgtgaaatccctatcagtgatagagact tataagttccctatcagtgatagagacaccaggaaacctgatcatgtagatcgaatggactctaaatccg ttcagccgggtcagattcccggggtttccggacaagtgcggtttttt SEQ ID No 36
H1 tRNA-A1 construct
aatatttgcatgtcgctatgtgttctgggaaatcaccataaacgtgaaatccctatcagtgatagagact tataagttccctatcagtgatagagacaccaggaaacctggtcatgtagatcgaatggactctaaatccg ttcagccgggttagattcccggggtttccggacaagtgcggtttttt SEQ ID No 37
H1 tRNA-A2 construct
aatatttgcatgtcgctatgtgttctgggaaatcaccataaacgtgaaatccctatcagtgatagagact tataagttccctatcagtgatagagacaccaggaaacctggtcaagtagatcgaatggactctaaatccg ttcagccgggttagattcccggggtttccggacaagtgcggtttttt SEQ ID No 38
H1 tRNA-A2B construct
aatatttgcatgtcgctatgtgttctgggaaatcaccataaacgtgaaatccctatcagtgatagagact tataagttccctatcagtgatagagacaccaggaaacctggtcaagtagatcgaatggactctaaatccg ttcagccgggtcagattcccggggtttccggacaagtgcggtttttt SEQ ID No 39
Terminator sequence used in the H1-tRNA constructs:
gacaagtgcggtttttt
                                                              SEQ ID No 40
M. Musculus tRNAglu coding sequence
tccctggtggtctagtggttaggattcggcgctctcaccgccgcggcccgggttcgattctcggtcaggg aa SEQ ID No 41
Mus musculus tRNA Glu with 5' and 3' non coding regions:
Gcctgtagtagtccgcggagcggaggttccaggcgggcaagcagtgtatctgccacggtggcggagagg ctgtgtgtctgagtgtctccaggagtcggtagccgtgacctcgggccgacgctccctggtggtctagtgg ttaggattcggcgctctcaccgccgcggcccgggttcgattctcggtcagggaagcctctcttcttcctc tctgcaccctcacttccccaaacctcgctcctcttccctcgctcacttttgcccaacaccaacgcacacc
```

```
                                                     SEQ ID No 42
1xtRNAglu-pyl DNA construct
gccgtgacctcgggccgacgctccctggtggtctagtggttaggattcggcgctctcaccgccgcggccc gggttcgattctcggtcagggaagcctctcccccaaacctcggaaacctgatcatgtagatcgaatggac tctaaatccgttcagccgggttagattcccggggtttccgcttcttcctcttttct SEQ ID No 43
3x tRNAglu-pyl: DNA construct including 3 repeats of the bicistronic
construct tRNAglu-tRNApyl
gccgtgacctcgggccgacgctccctggtggtctagtggttaggattcggcgctctcaccgccgcggccc gggttcgattctcggtcagggaagcctctcccccaaacctcggaaacctgatcatgtagatcgaatggac tctaaatccgttcagccgggttagattcccggggtttccgcttcttcctcttttctgcaccctcacttca gctgagccgtgacctcgggccgacgctccctggtggtctagtggttaggattcggcgctctcaccgccgc ggcccggggttcgattctcggtcagggaagcctctcccccaaacctcggaaacctgatcatgtagatcgaa tggactctaaatccgttcagccgggttagattcccggggtttccgcttcttcctcttttctgcaccccaa tattgccgtgacctcgggccgacgctccctggtggtctagtggttaggattcggcgctctcaccgccgcg gcccgggttcgattctcggtcagggaagcctctcccccaaacctcggaaacctgatcatgtagatcgaat ggactctaaatccgttcagccgggttagattcccggggtttccgtagcgtccttttggaaagacaagtg ggtggcgaattcgatatc SEQ ID No 44
5'Leader sequence for tRNAglu-pyl constructs
gccgtgacctcgggccgacgc SEQ ID No 45
Terminator sequence used in the tRNAglu-pyl constructs
tagcgtccttttg SEQ ID No 46
Terminator sequence used in the tRNAglu-pyl constructs
Cttcttcctcttttct SEQ ID No 47
Intergene sequence used in the tRNAglu-pyl constructs
gcctctcccccaaacctc SEQ ID No 48
M. Musculus tRNAasp coding sequence
Tcctcgttagtatagtggtgagtatccccgcctgtcacccgcgagaccggcgttccattccccgacgggg ag SEQ ID No 49
M. musculus tRNA Asp with upstream and downstream regions
tgggtgagacgaggttgtgggtcgtgtgtgtcgtcgtagacggtcgggcgacggtgcgtcgtagtcggc gttgtcctcgttagtatagtggtgagtatccccgcctgtcacccgcgagaccggcgttccattccccgac ggggagacgtagcgtccttttggaaagacaagtgggtggcccgcggg SEQ ID No 50
1x tRNAasp-pyl DNA construct
ggtgcgtcgtagtcggcgttgtcctcgttagtatagtggtgagtatccccgcctgtcacccgcgagaccg gcgttccattccccgacggggagacgtagccccacctcggaaacctgatcatgtagatcgaatggactct aaatccgttcagccgggttagattcccggggtttccg SEQ ID No 51
2x tRNAasp-pyl: DNA construct including 2 repeats of the bicistronic
construct tRNAasp-pyl
tcctcgttagtatagtggtgagtatccccgcctgtcacccgcgagaccggcgttccattccccgacgggg agacgtagcccacctcggaaacctgatcatgtagatcgaatggactctaaatccgttcagccgggttag attcccggggtttccgtagcgtccttttggaaagacaaggtgcgtcgtagtcggcgttgtcctcgttag
```

```
                                                     -continued
tatagtggtgagtatccccgcctgtcacccgcgagaccggcgttccattccccgacggggagacgtagcc ccacctcggaaacctgatcatgtagatcgaatggactctaaatccgttcagccgggttagattcccgggg tttccgtagcgtcctttt
```

SEQ ID No 52

Leader sequence used in the 2xAsp-pyl construct
Ggtgcgtcgtagtcggcgttg

SEQ ID No 53

Terminator sequence used in the 2xAsp-pyl construct
tagcgtccttttt

SEQ ID No 54 intergene sequence used in the tRNAasp-pyl constructs
acgtagccccacctc

SEQ ID No 55 human tRNAglu coding sequence
TCCCTGGTGGTCTAGTGGCTAGGATTCGGCGCTTTCACCGCCGCGGCCCGGGTTCGATTCCCGGTCAGGA

AT

SEQ ID No 56 human tRNAasp coding sequence
TCCTTGTTAGTATAGTGGTGAGTGTTTCTGCCTGTCATGTGGAGACTGGAGTTTGAGTCCCCAACAGGGA SEQ ID No 57

7SL promoter variant: 7SL-1
CGCTCCCCAATGACGTAACTGCCCTGC-AGCTTCTAGTAGCT-TTTCGCAGCGTCTCCGACCG SEQ ID No 58

7SL promoter variant: 7SL-2
TCTGGTTGCTACCATGTGTAGCC-TGCAAGCCTCTAGCAGCTCTTTTGCAGCGACGCCGACCG SEQ ID No 59

7SL promoter variant: SL28
TAACATTGCTAATGAGTTTTGGGCACACATTGTCATTGATAACATCTTATCAGGAGACAGGG SEQ ID No 60

7SL promoter variant: 7L63
ACAGAGGAACTACCATAACAAGAACCAAAGAGAAATGGCAtACcTCAGG

SEQ ID No 61

7SL promoter variant: 7L23
CTCCCTCTCAAAACTCAAGGAAATCTAGTGGGCATGGTGCACAT

SEQ ID No 62

7SL promoter variant: 7L7
AGGTACTACCCAATGGTTTTCTAAAATACTTGCATC-TGCACATGCCATG

SEQ ID No 63

EBER promoter variant: EBER1
GATCCAAACTTTTGTTTTAG GATTTATGCA TCCATTATCC CGCAGTTCCA CCTAAACGGG

GCTTAACGTT GCATCCCAGA AGATGCACGC TTAACCCCGC CTACAACCGT GACGTAGCTG

TTTACCAGCA TGTATAGAGT TACGGTTCGC TACATCAAAC

SEQ ID No 64

Vault promoter variant: Hvg3
aggtcgctgagtcaagctaaagcaccgttgttttgactcactctttgtgacgtaggtctttctcaccagt caagaaaatacaatccgaaagcaacctctg SEQ ID No 65

Vault promoter variant: Hvg2
Tggttgctgagtcatgctaaaacactgttgttttgactcactttgtgacgtaggtctttctcaccagtca agaaaatataatccggagatagcctctg SEQ ID No 66

Methanosarcina mazei pylRS aa sequence
Mdkkpintlisatglwmsrtgtihkikhhevsrskiyiemacgdhlvvnnsrssrtaralrhhkyrktck rcrvsdedlnkfltkanedgtsvkvkvvsaptrtkkampksvarapkplenteaagagpsgskfspaipv stgesysvpasystsissistgatasalvkgntnpitsmsapvgasapaltksqtdrlevllnpkdeisl nsgkpfrelesellsrrkkdlgqiyaeerenylgklereitrffvdrgfleikspilipleyiermgidn -continued dtelskgifrvdknfclrpmlapnlynylrkldralpdpikifeigpcyrkesdgkehleeftmlnfcgm gsgctrenlesiitdflnhlgidfkivgdscmvygdtldvmhgdlelssavvgpipldrewgidkpwiga gfglerllkvkhdfknikraarsesyyngistnl SEQ ID No 67
Methanosarcina mazei pylRS nucleotide sequence
atggataaaaaaccattgaatacgctcattagcgcaactgggctgtggatgagccgtacgggaacgattc ataaaatcaagcaccacgaagtatctcgtagcaaaatctatatcgagatggcttgcggcgaccatctcgt ggtaaacaatagcaggtcctcacggaccgcccgtgccttgcgccaccacaaatatcgtaaaacttgtaag agatgtagagtgagcgacgaggatctgaacaagtttcttacaaaggccaacgaggaccaaaccagcgtca aagtcaaggttgtgagcgccccaacacgcaccaagaaggccatgcccaagtctgttgcgcgggcaccgaa acctctggagaatactgaggccgctcaggcccagcccagcggttcaaaattctctcctgccattccagtt agcactcaagagtcagtcagcgtgcccgcctctgtgtctacatccatcagctctatctccaccggcgcaa cagcctctgccctggtgaagggtaatacgaaccctatcacgagtatgtccgcacccgtgcaagcaagtgc tcccgcactcactaaatcccaaacggaccggctggaggtcctgcttaaccctaaggatgaaatcagcctg aacagtggaaaaccgtttcgagaactggaatccgagctcttaagccggcgaaagaaagatttgcaacaga tttacgccgaagaacgggaaaattatctgggcaagctggagagagaaatcactaggttctttgtagatag gggctttctggagattaagagtcccatattgatccctctcgaatacattgagcgtatgggcatcgacaac gacacagaacttagcaagcagatctttcgggtggacaaaaacttctgcctcaggcctatgctggctccaa atctgtacaactatcttaggaaactcgaccgggccctgcccgatcccattaaaatcttcgaaattggacc ttgctatagaaaggagagcgatggcaaggagcacctggaggagtttactatgctcaatttctgtcaaatg ggctccggctgcacacgtgagaacctcgaatccattataaccgacttcctgaatcacctggggattgatt tcaagatcgtgggcgactcctgcatggtgtttggtgatacgttggatgtgatgcacggagatttggaatt gtcaagcgctgtggtaggcccattcctctcgacagggagtggggtattgacaagccctggatcggcgca ggttttggactggagcgcctgttgaaggttaagcatgacttcaaaaacataaagagagccgcacgcagcg aatcctattataatggaatcagcactaacttgtaa Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims:

---

The invention claimed is:

1. A DNA construct which comprises a tRNApyl gene comprising a tRNApyl coding sequence comprising a functional intragenic RNA polymerase III promoter element comprising a putative A box, a putative B box, or a combination thereof, wherein the tRNApyl gene is capable of expressing functional tRNApyl sufficiently to support amber suppression in a eukaryotic expression system wherein the tRNApyl gene comprises a nucleic acid sequence selected from SEQ ID Nos 7, 8, 9, 10, and 11 derived from *Methanosarcina mazei* or a sequence of an analogous tRNApyl gene derived from another bacterial species which comprises 1 or 2 mutations in the putative A box, 1 or 2 mutations in the putative B box, or a combination thereof made in positions equivalent to A10G, A52C, T14A, or a combination thereof as shown in SEQ ID Nos 7, 8, 9, 10, or 11, wherein the mutations result in the generation of the functional intragenic promoter element.

2. A DNA construct according to claim 1 comprising a terminator sequence which is downstream of the tRNApyl coding sequence.

3. A DNA construct according to claim 1 wherein the tRNApyl coding sequence is operably linked to a 5' promoter element comprising a RNA polymerase III promoter placed 5' to the tRNApyl coding sequence.

4. A DNA construct according to claim 3 wherein the 5' promoter element and the tRNApyl coding sequence are separated by a spacer sequence containing a transcriptional start site.

5. A DNA construct according to claim 1 which comprises the functional intragenic RNA polymerase III promoter element and a 5' promoter element comprising a RNA polymerase III promoter sequence placed 5' to the tRNApyl coding sequence such that the intragenic promoter element and the 5' promoter element constitute a hybrid promoter.

6. A DNA construct according to claim 5 wherein the 5' promoter element is a 5' element of a Type 4 RNA polymerase III promoter.

7. A DNA construct according to claim 6 wherein the 5' promoter element of the Type 4 RNA Polymerase III promoter is selected from:
(a) 5' promoter elements of an EBER RNA gene promoter,
(b) a 7SL RNA gene promoter,
(c) a Vault RNA gene promoter; and
(d) SEQ ID Nos 12, 20, 26, 57, 58, 59, 60, 61, 62, 63, 64 and 65.

8. A DNA construct according to claim 7 wherein the 5' promoter element of the Type 4 RNA Polymerase III promoter is a 7SL RNA gene promoter and wherein the DNA construct further comprises a spacer sequence selected from SEQ ID NOs 13 and 21.

9. A DNA construct according to claim 7 wherein the 5' promoter element is selected from SEQ ID Nos 12, 20, 26, 57, 58, 59, 60, 61, 62, 63, 64 and 65.

10. A DNA construct according to claim 5 wherein the 5' promoter element and the tRNApyl coding sequence are separated by a spacer sequence containing a transcriptional start site, and wherein the DNA construct further comprises a PylRS coding sequence or gene.

11. A multimeric DNA construct comprising multiple copies of the DNA construct according to claim 1.

12. A DNA construct according to claim 1 which further comprises a PylRS coding sequence or gene.

13. A DNA construct according to claim 1, wherein the mutations in the 1 or 2 nucleotide positions of the putative A box, the putative B box, or combinations thereof are selected from: (a) A10G, T14A, A52C, and combinations thereof in a tRNApyl gene from *Methanosarcina mazei* (SEQ ID NO: 3), and (b) mutations in positions equivalent to A10G, T14A and A52C in an analogous tRNApyl gene derived from another bacterial species selected from the group consisting of *Methanosarcina barkeri* (SEQ ID NO: 1), *Desulfitobacterium hafniense* (SEQ ID NO: 5), *Methanosarcina acetivorans* (SEQ ID NO: 2), *Methanosarcina burtonii* (SEQ ID NO: 4) and *Methanosarcina thermophila*.

14. A eukaryotic cell line comprising the DNA construct of claim 1, wherein the eukaryotic cell line expresses functional PylRS and functional tRNApyl in which functional tRNApyl expression occurs under the control of the intragenic promoter element and a 5' promoter element comprising a RNA polymerase III promoter element placed 5' to the tRNApyl coding sequence such that the intragenic promoter element and 5' promoter element constitute a hybrid promoter sufficient to support amber suppression.

15. A process for preparing a target protein containing one or more non-natural amino acids encoded by an amber codon which comprises expressing said target protein in a eukaryotic cell line which is transformed with a gene encoding said target protein and the DNA construct according to claim 1, such that tRNApyl is expressed and functions sufficiently to support amber suppression.

16. A process for preparing a chemically modified target protein which comprises preparing a target protein according to the process of claim 15 and chemically modifying the resultant target protein.

17. A process according to claim 15 wherein at least one of the non-natural amino acids comprises an alkyne or azide moiety.

* * * * *

SEQUENCE LISTING

```
<160> NUMBER OF SEQ ID NOS: 81

<210> SEQ ID NO 1
<211> LENGTH: 65
<212> TYPE: DNA
<213> ORGANISM: Methanosarcina barkeri

<400> SEQUENCE: 1
ggaaacctga tcatgtagat cgtggacttc taaatccgca gccgggtaga ttcccggggt    60
ttccg                                                                 65

<210> SEQ ID NO 2
<211> LENGTH: 69
```

```
<212> TYPE: DNA
<213> ORGANISM: Methanosarcina acetivorans

<400> SEQUENCE: 2
ggaaacctga tcatgtagat cgaatggact ctaaatccgt tcagccgggt tagattcccg    60
gggtttccg                                                             69

<210> SEQ ID NO 3
<211> LENGTH: 69
<212> TYPE: DNA
<213> ORGANISM: Methanosarcina mazei

<400> SEQUENCE: 3
ggaaacctga tcatgtagat cgaatggact ctaaatccgt tcagccgggt tagattcccg    60
gggtttccg                                                             69

<210> SEQ ID NO 4
<211> LENGTH: 69
<212> TYPE: DNA
<213> ORGANISM: Methanococcoides burtonii

<400> SEQUENCE: 4
ggagacttga tcatgtagat cgaacggact ctaaatcctt tcagccgggt tagattcccg    60
gagtttccg                                                             69

<210> SEQ ID NO 5
<211> LENGTH: 64
<212> TYPE: DNA
<213> ORGANISM: Desulfobacterium hafniense

<400> SEQUENCE: 5
ggaaacctga tcatgtagat cgtggactct aaatccgcag ccgggtagat tcccggggtt    60
tccg                                                                  64

<210> SEQ ID NO 6
<211> LENGTH: 18
<212> TYPE: DNA
<213> ORGANISM: Artificial sequence
<220> FEATURE:
<223> OTHER INFORMATION: Synthetic sequence: Terminator sequence used
      for WT and mutant A - box and/or B-box tRNApyl constructs

<400> SEQUENCE: 6
gacaagtgcg gttttttt                                                   18

<210> SEQ ID NO 7
<211> LENGTH: 69
<212> TYPE: DNA
<213> ORGANISM: Artificial sequence
<220> FEATURE:
<223> OTHER INFORMATION: Synthetic sequence: tRNApyl Methanosarcina
      mazei A10G mutation ('tRNA-A1'); coding sequence

<400> SEQUENCE: 7
ggaaacctgg tcatgtagat cgaatggact ctaaatccgt tcagccgggt tagattcccg    60
gggtttccg                                                             69

<210> SEQ ID NO 8
<211> LENGTH: 69
<212> TYPE: DNA
<213> ORGANISM: Artificial sequence
<220> FEATURE:
```

<223> OTHER INFORMATION: Synthetic sequence: tRNApyl Methanosarcina
      mazei A10G A52C mutation ('tRNA-A1B'); coding sequence

<400> SEQUENCE: 8
ggaaacctgg tcatgtagat cgaatggact ctaaatccgt tcagccgggt tcgattcccg      60
gggtttccg                                                             69

<210> SEQ ID NO 9
<211> LENGTH: 69
<212> TYPE: DNA
<213> ORGANISM: Artificial sequence
<220> FEATURE:
<223> OTHER INFORMATION: Synthetic sequence: tRNApyl Methanosarcina
      mazei A52C mutation ('tRNA-B'); coding sequence

<400> SEQUENCE: 9
ggaaacctga tcatgtagat cgaatggact ctaaatccgt tcagccgggt tcgattcccg      60
gggtttccg                                                             69

<210> SEQ ID NO 10
<211> LENGTH: 69
<212> TYPE: DNA
<213> ORGANISM: Artificial sequence
<220> FEATURE:
<223> OTHER INFORMATION: Synthetic sequence: tRNApyl Methanosarcina
      mazei A10G, T14A, A52C mutations ('tRNA-A2B'); coding sequence

<400> SEQUENCE: 10
ggaaacctgg tcaagtagat cgaatggact ctaaatccgt tcagccgggt tcgattcccg      60
gggtttccg                                                             69

<210> SEQ ID NO 11
<211> LENGTH: 69
<212> TYPE: DNA
<213> ORGANISM: Artificial sequence
<220> FEATURE:
<223> OTHER INFORMATION: Synthetic sequence: tRNApyl Methanosarcina
      mazei A52C, T14A, mutations ('tRNA-A2'); coding sequence

<400> SEQUENCE: 11
ggaaacctga tcaagtagat cgaatggact ctaaatccgt tcagccgggt tcgattcccg      60
gggtttccg                                                             69

<210> SEQ ID NO 12
<211> LENGTH: 60
<212> TYPE: DNA
<213> ORGANISM: Homo sapiens

<400> SEQUENCE: 12
cccagttgat gacgtcacca taccacagct tctagtgcta ttctgcgccg gtatccgacc      60

<210> SEQ ID NO 13
<211> LENGTH: 4
<212> TYPE: DNA
<213> ORGANISM: Artificial sequence
<220> FEATURE:
<223> OTHER INFORMATION: Synthetic sequence: Spacer used in 7SL
      constructs

<400> SEQUENCE: 13 acca                                                                   4

<210> SEQ ID NO 14

```
<211> LENGTH: 149
<212> TYPE: DNA
<213> ORGANISM: Artificial sequence
<220> FEATURE:
<223> OTHER INFORMATION: Synthetic sequence: 7SL tRNA-WT construct

<400> SEQUENCE: 14
cccagttgat gacgtcacca taccacagct tctagtgcta ttctgcgccg gtatccgacc      60
accaggaaac ctgatcatgt agatcgaatg gactctaaat ccgttcagcc gggttagatt     120
cccggggttt ccggacaagt gcggtttt                                        149

<210> SEQ ID NO 15
<211> LENGTH: 149
<212> TYPE: DNA
<213> ORGANISM: Artificial sequence
<220> FEATURE:
<223> OTHER INFORMATION: Synthetic sequence: 7SL tRNA-B construct

<400> SEQUENCE: 15
cccagttgat gacgtcacca taccacagct tctagtgcta ttctgcgccg gtatccgacc      60
accaggaaac ctgatcatgt agatcgaatg gactctaaat ccgttcagcc gggttcgatt     120
cccggggttt ccggacaagt gcggtttt                                        149

<210> SEQ ID NO 16
<211> LENGTH: 149
<212> TYPE: DNA
<213> ORGANISM: Artificial sequence
<220> FEATURE:
<223> OTHER INFORMATION: Synthetic sequence: 7SL tRNA-A1 construct

<400> SEQUENCE: 16
cccagttgat gacgtcacca taccacagct tctagtgcta ttctgcgccg gtatccgacc      60
accaggaaac ctggtcatgt agatcgaatg gactctaaat ccgttcagcc gggttagatt     120
cccggggttt ccggacaagt gcggtttt                                        149

<210> SEQ ID NO 17
<211> LENGTH: 149
<212> TYPE: DNA
<213> ORGANISM: Artificial sequence
<220> FEATURE:
<223> OTHER INFORMATION: Synthetic sequence: 7SL tRNA-AB construct

<400> SEQUENCE: 17
cccagttgat gacgtcacca taccacagct tctagtgcta ttctgcgccg gtatccgacc      60
accaggaaac ctggtcatgt agatcgaatg gactctaaat ccgttcagcc gggttcgatt     120
cccggggttt ccggacaagt gcggtttt                                        149

<210> SEQ ID NO 18
<211> LENGTH: 149
<212> TYPE: DNA
<213> ORGANISM: Artificial sequence
<220> FEATURE:
<223> OTHER INFORMATION: Synthetic sequence: 7SL tRNA-A2B construct

<400> SEQUENCE: 18
cccagttgat gacgtcacca taccacagct tctagtgcta ttctgcgccg gtatccgacc      60
accaggaaac ctggtcaagt agatcgaatg gactctaaat ccgttcagcc gggttcgatt     120
cccggggttt ccggacaagt gcggtttt                                        149
```

```
<210> SEQ ID NO 19
<211> LENGTH: 16
<212> TYPE: DNA
<213> ORGANISM: Artificial sequence
<220> FEATURE:
<223> OTHER INFORMATION: Synthetic sequence: Terminator sequence used
      in the 7SL, Vault, EBER constructs

<400> SEQUENCE: 19
gacaagtgcg gttttt                                                      16

<210> SEQ ID NO 20
<211> LENGTH: 98
<212> TYPE: DNA
<213> ORGANISM: Homo sapiens

<400> SEQUENCE: 20
tggtcgctga gtcatgctga agcactctct ttttgactca ctctttgtga cgtaggtctt      60
tctcaccagt caataaaata taatccgaaa gcaacctc                              98

<210> SEQ ID NO 21
<211> LENGTH: 6
<212> TYPE: DNA
<213> ORGANISM: Artificial sequence
<220> FEATURE:
<223> OTHER INFORMATION: Synthetic sequence: Spacer used for Vault-tRNA
      constructs

<400> SEQUENCE: 21 ccacca                                                                 6

<210> SEQ ID NO 22
<211> LENGTH: 189
<212> TYPE: DNA
<213> ORGANISM: Artificial sequence
<220> FEATURE:
<223> OTHER INFORMATION: Synthetic sequence: Vault tRNA-WT construct

<400> SEQUENCE: 22
tggtcgctga gtcatgctga agcactctct ttttgactca ctctttgtga cgtaggtctt      60
tctcaccagt caataaaata taatccgaaa gcaacctccc accaggaaac ctgatcatgt     120
agatcgaatg gactctaaat ccgttcagcc gggttagatt cccggggttt ccggacaagt     180
gcggtttt                                                             189

<210> SEQ ID NO 23
<211> LENGTH: 189
<212> TYPE: DNA
<213> ORGANISM: Artificial sequence
<220> FEATURE:
<223> OTHER INFORMATION: Synthetic sequence: Vault tRNA-B construct

<400> SEQUENCE: 23
tggtcgctga gtcatgctga agcactctct ttttgactca ctctttgtga cgtaggtctt      60
tctcaccagt caataaaata taatccgaaa gcaacctccc accaggaaac ctgatcatgt     120
agatcgaatg gactctaaat ccgttcagcc gggttcgatt cccggggttt ccggacaagt     180
gcggtttt                                                             189

<210> SEQ ID NO 24
<211> LENGTH: 189
<212> TYPE: DNA
<213> ORGANISM: Artificial sequence
<220> FEATURE:
```

<223> OTHER INFORMATION: Synthetic sequence: Vault tRNA-AB construct

<400> SEQUENCE: 24
tggtcgctga gtcatgctga agcactctct ttttgactca ctctttgtga cgtaggtctt    60
tctcaccagt caataaaata taatccgaaa gcaacctccc accaggaaac ctggtcatgt   120
agatcgaatg gactctaaat ccgttcagcc gggttcgatt cccggggttt ccggacaagt   180
gcggttttt                                                           189

<210> SEQ ID NO 25
<211> LENGTH: 189
<212> TYPE: DNA
<213> ORGANISM: Artificial sequence
<220> FEATURE:
<223> OTHER INFORMATION: Synthetic sequence: Vault tRNA-A2B construct

<400> SEQUENCE: 25
tggtcgctga gtcatgctga agcactctct ttttgactca ctctttgtga cgtaggtctt    60
tctcaccagt caataaaata taatccgaaa gcaacctccc accaggaaac ctggtcaagt   120
agatcgaatg gactctaaat ccgttcagcc gggttcgatt cccggggttt ccggacaagt   180
gcggttttt                                                           189

<210> SEQ ID NO 26
<211> LENGTH: 80
<212> TYPE: DNA
<213> ORGANISM: Epstein-Barr virus

<400> SEQUENCE: 26
agatgcacgc ttaaccccgc ctacaaccgt gacgtagctg tttaccagca tgtatagagt    60
tacggttcgc tacatcaaac                                                80

<210> SEQ ID NO 27
<211> LENGTH: 4
<212> TYPE: DNA
<213> ORGANISM: Artificial sequence
<220> FEATURE:
<223> OTHER INFORMATION: Synthetic sequence: Spacer used in EBER
      constructs

<400> SEQUENCE: 27 acca                                                                 4

<210> SEQ ID NO 28
<211> LENGTH: 170
<212> TYPE: DNA
<213> ORGANISM: Artificial sequence
<220> FEATURE:
<223> OTHER INFORMATION: Synthetic sequence: EBER2 tRNA-WT construct

<400> SEQUENCE: 28
agatgcacgc ttaaccccgc ctacaaccgt gacgtagctg tttaccagca tgtatagagt    60
tacggttcgc tacatcaaac accaggaaac ctgatcatgt agatcgaatg gactctaaat   120
ccgttcagcc gggttagatt cccggggttt ccgggacaag tgcggttttt              170

<210> SEQ ID NO 29
<211> LENGTH: 170
<212> TYPE: DNA
<213> ORGANISM: Artificial sequence
<220> FEATURE:
<223> OTHER INFORMATION: Synthetic sequence: EBER2 tRNA-B construct

<400> SEQUENCE: 29

```
agatgcacgc ttaaccccgc ctacaaccgt gacgtagctg tttaccagca tgtatagagt      60
tacggttcgc tacatcaaac accaggaaac ctgatcatgt agatcgaatg gactctaaat     120
ccgttcagcc gggttcgatt cccggggttt ccgggacaag tgcggttttt                170
```

<210> SEQ ID NO 30
<211> LENGTH: 170
<212> TYPE: DNA
<213> ORGANISM: Artificial sequence
<220> FEATURE:
<223> OTHER INFORMATION: Synthetic sequence: EBER2 tRNA-A1 construct

<400> SEQUENCE: 30

```
agatgcacgc ttaaccccgc ctacaaccgt gacgtagctg tttaccagca tgtatagagt      60
tacggttcgc tacatcaaac accaggaaac ctggtcatgt agatcgaatg gactctaaat     120
ccgttcagcc gggttagatt cccggggttt ccgggacaag tgcggttttt                170
```

<210> SEQ ID NO 31
<211> LENGTH: 170
<212> TYPE: DNA
<213> ORGANISM: Artificial sequence
<220> FEATURE:
<223> OTHER INFORMATION: Synthetic sequence: EBER2 tRNA-A1B construct

<400> SEQUENCE: 31

```
agatgcacgc ttaaccccgc ctacaaccgt gacgtagctg tttaccagca tgtatagagt      60
tacggttcgc tacatcaaac accaggaaac ctggtcatgt agatcgaatg gactctaaat     120
ccgttcagcc gggttcgatt cccggggttt ccgggacaag tgcggttttt                170
```

<210> SEQ ID NO 32
<211> LENGTH: 170
<212> TYPE: DNA
<213> ORGANISM: Artificial sequence
<220> FEATURE:
<223> OTHER INFORMATION: Synthetic sequence: EBER2 tRNA-A2B construct

<400> SEQUENCE: 32

```
agatgcacgc ttaaccccgc ctacaaccgt gacgtagctg tttaccagca tgtatagagt      60
tacggttcgc tacatcaaac accaggaaac ctggtcaagt agatcgaatg gactctaaat     120
ccgttcagcc gggttcgatt cccggggttt ccgggacaag tgcggttttt                170
```

<210> SEQ ID NO 33
<211> LENGTH: 101
<212> TYPE: DNA
<213> ORGANISM: Homo sapiens

<400> SEQUENCE: 33

```
aatatttgca tgtcgctatg tgttctggga aatcaccata aacgtgaaat ccctatcagt      60
gatagagact tataagttcc ctatcagtga tagagacacc a                         101
```

<210> SEQ ID NO 34
<211> LENGTH: 188
<212> TYPE: DNA
<213> ORGANISM: Artificial sequence
<220> FEATURE:
<223> OTHER INFORMATION: Synthetic sequence: H1 tRNA-WT construct

<400> SEQUENCE: 34

```
aatatttgca tgtcgctatg tgttctggga aatcaccata aacgtgaaat ccctatcagt      60
```

```
gatagagact tataagttcc ctatcagtga tagagacacc aggaaacctg atcatgtaga        120
tcgaatggac tctaaatccg ttcagccggg ttagattccc ggggtttccg gacaagtgcg        180
gttttttt                                                                188

<210> SEQ ID NO 35
<211> LENGTH: 188
<212> TYPE: DNA
<213> ORGANISM: Artificial sequence
<220> FEATURE:
<223> OTHER INFORMATION: Synthetic sequence: H1 tRNA-B construct

<400> SEQUENCE: 35
aatatttgca tgtcgctatg tgttctggga aatcaccata aacgtgaaat ccctatcagt        60
gatagagact tataagttcc ctatcagtga tagagacacc aggaaacctg atcatgtaga        120
tcgaatggac tctaaatccg ttcagccggg tcagattccc ggggtttccg gacaagtgcg        180
gttttttt                                                                188

<210> SEQ ID NO 36
<211> LENGTH: 188
<212> TYPE: DNA
<213> ORGANISM: Artificial sequence
<220> FEATURE:
<223> OTHER INFORMATION: Synthetic sequence: H1 tRNA-A1 construct

<400> SEQUENCE: 36
aatatttgca tgtcgctatg tgttctggga aatcaccata aacgtgaaat ccctatcagt        60
gatagagact tataagttcc ctatcagtga tagagacacc aggaaacctg gtcatgtaga        120
tcgaatggac tctaaatccg ttcagccggg ttagattccc ggggtttccg gacaagtgcg        180
gttttttt                                                                188

<210> SEQ ID NO 37
<211> LENGTH: 188
<212> TYPE: DNA
<213> ORGANISM: Artificial sequence
<220> FEATURE:
<223> OTHER INFORMATION: Synthetic sequence: H1 tRNA-A2 construct

<400> SEQUENCE: 37
aatatttgca tgtcgctatg tgttctggga aatcaccata aacgtgaaat ccctatcagt        60
gatagagact tataagttcc ctatcagtga tagagacacc aggaaacctg gtcaagtaga        120
tcgaatggac tctaaatccg ttcagccggg ttagattccc ggggtttccg gacaagtgcg        180
gttttttt                                                                188

<210> SEQ ID NO 38
<211> LENGTH: 188
<212> TYPE: DNA
<213> ORGANISM: Artificial sequence
<220> FEATURE:
<223> OTHER INFORMATION: Synthetic sequence: H1 tRNA-A2B construct

<400> SEQUENCE: 38
aatatttgca tgtcgctatg tgttctggga aatcaccata aacgtgaaat ccctatcagt        60
gatagagact tataagttcc ctatcagtga tagagacacc aggaaacctg gtcaagtaga        120
tcgaatggac tctaaatccg ttcagccggg tcagattccc ggggtttccg gacaagtgcg        180
gttttttt                                                                188
```

<210> SEQ ID NO 39
<211> LENGTH: 18
<212> TYPE: DNA
<213> ORGANISM: Artificial sequence
<220> FEATURE:
<223> OTHER INFORMATION: Synthetic sequence: Terminator sequence used
      in the H1-tRNA constructs

<400> SEQUENCE: 39
gacaagtgcg gtttttt                                                    18

<210> SEQ ID NO 40
<211> LENGTH: 72
<212> TYPE: DNA
<213> ORGANISM: Mus musculus

<400> SEQUENCE: 40
tccctggtgg tctagtggtt aggattcggc gctctcaccg ccgcggcccg ggttcgattc      60
tcggtcaggg aa                                                         72

<210> SEQ ID NO 41
<211> LENGTH: 280
<212> TYPE: DNA
<213> ORGANISM: Mus musculus

<400> SEQUENCE: 41
gcctgtagta gtccgccgga gcggaggttc caggcgggca agcagtgtat ctgccacggt      60
ggcggagagg ctgtgtgtct gagtgtctcc aggagtcggt agccgtgacc tcgggccgac     120
gctccctggt ggtctagtgg ttaggattcg gcgctctcac cgccgcggcc cgggttcgat     180
tctcggtcag ggaagcctct cttcttcctc tctgcaccct cacttcccca aacctcgctc     240
ctcttccctc gctcactttt gcccaacacc aacgcacacc                           280

<210> SEQ ID NO 42
<211> LENGTH: 196
<212> TYPE: DNA
<213> ORGANISM: Artificial sequence
<220> FEATURE:
<223> OTHER INFORMATION: Synthetic sequence: 1xtRNAglu-pyl DNA construct

<400> SEQUENCE: 42
gccgtgacct cgggccgacg ctccctggtg gtctagtggt taggattcgg cgctctcacc      60
gccgcggccc gggttcgatt ctcggtcagg gaagcctctc cccaaacct cggaaacctg     120 atcatgtaga tcgaatggac tctaaatccg ttcagccggg ttagattccc ggggtttccg     180
cttcttcctc ttttct                                                    196

<210> SEQ ID NO 43
<211> LENGTH: 648
<212> TYPE: DNA
<213> ORGANISM: Artificial sequence
<220> FEATURE:
<223> OTHER INFORMATION: Synthetic sequence: 3x tRNAglu-pyl: DNA construct including 3
      repeats of the bicistronic construct tRNAglu-tRNApyl

<400> SEQUENCE: 43
gccgtgacct cgggccgacg ctccctggtg gtctagtggt taggattcgg cgctctcacc      60
gccgcggccc gggttcgatt ctcggtcagg gaagcctctc cccaaacct cggaaacctg     120 atcatgtaga tcgaatggac tctaaatccg ttcagccggg ttagattccc ggggtttccg     180
cttcttcctc ttttctgcac cctcacttca gctgagccgt gacctcgggc cgacgctccc     240

```
tggtggtcta gtggttagga ttcggcgctc tcaccgccgc ggcccgggtt cgattctcgg    300
tcagggaagc ctctccccca aacctcggaa acctgatcat gtagatcgaa tggactctaa    360
atccgttcag ccgggttaga ttcccggggt ttccgcttct tcctcttttc tgcacccccaa   420 tattgccgtg acctcgggcc gacgctccct ggtggtctag tggttaggat tcggcgctct    480
caccgccgcg gcccgggttc gattctcggt cagggaagcc tctcccccaa acctcggaaa    540
cctgatcatg tagatcgaat ggactctaaa tccgttcagc cgggttagat tcccggggtt    600
tccgtagcgt ccttttttgga aagacaagtg ggtggcgaat tcgatatc                648
```

<210> SEQ ID NO 44
<211> LENGTH: 21
<212> TYPE: DNA
<213> ORGANISM: Artificial sequence
<220> FEATURE:
<223> OTHER INFORMATION: Synthetic sequence: 5' Leader sequence for tRNAglu-pyl constructs

<400> SEQUENCE: 44

```
gccgtgacct cgggccgacg c                                               21
```

<210> SEQ ID NO 45
<211> LENGTH: 14
<212> TYPE: DNA
<213> ORGANISM: Artificial sequence
<220> FEATURE:
<223> OTHER INFORMATION: Synthetic sequence: Terminator sequence used in the tRNAglu-pyl constructs

<400> SEQUENCE: 45

```
tagcgtcctt tttg                                                       14
```

<210> SEQ ID NO 46
<211> LENGTH: 16
<212> TYPE: DNA
<213> ORGANISM: Artificial sequence
<220> FEATURE:
<223> OTHER INFORMATION: Synthetic sequence: Terminator sequence used in the tRNAglu-pyl constructs

<400> SEQUENCE: 46

```
cttcttcctc ttttct                                                     16
```

<210> SEQ ID NO 47
<211> LENGTH: 18
<212> TYPE: DNA
<213> ORGANISM: Artificial sequence
<220> FEATURE:
<223> OTHER INFORMATION: Synthetic sequence: Intergene sequence used in the tRNAglu-pyl constructs

<400> SEQUENCE: 47

```
gcctctcccc caaacctc                                                   18
```

<210> SEQ ID NO 48
<211> LENGTH: 72
<212> TYPE: DNA
<213> ORGANISM: Mus musculus

<400> SEQUENCE: 48

```
tcctcgttag tatagtggtg agtatccccg cctgtcaccc gcgagaccgg cgttccattc    60
cccgacgggg ag                                                         72
```

```
<210> SEQ ID NO 49
<211> LENGTH: 188
<212> TYPE: DNA
<213> ORGANISM: Mus musculus

<400> SEQUENCE: 49
tgggtgagac ggaggttgtg ggtcgtgtgt gtcgtcgtag acggtcgggc gacggtgcgt    60
cgtagtcggc gttgtcctcg ttagtatagt ggtgagtatc cccgcctgtc acccgcgaga   120
ccggcgttcc attcccgac ggggagacgt agcgtccttt ttggaaagac aagtgggtgg   180
cccgcggg                                                            188

<210> SEQ ID NO 50
<211> LENGTH: 177
<212> TYPE: DNA
<213> ORGANISM: Artificial sequence
<220> FEATURE:
<223> OTHER INFORMATION: Synthetic sequence: 1x tRNAasp-pyl DNA
      construct

<400> SEQUENCE: 50
ggtgcgtcgt agtcggcgtt gtcctcgtta gtatagtggt gagtatcccc gcctgtcacc    60
cgcgagaccg gcgttccatt ccccgacggg gagacgtagc cccacctcgg aaacctgatc   120
atgtagatcg aatggactct aaatccgttc agccgggtta gattcccggg gtttccg      177

<210> SEQ ID NO 51
<211> LENGTH: 369
<212> TYPE: DNA
<213> ORGANISM: Artificial sequence
<220> FEATURE:
<223> OTHER INFORMATION: Synthetic sequence: 2x tRNAasp-pyl: DNA
      construct including 2 repeats of the bicistronic construct
      tRNAasp-pyl

<400> SEQUENCE: 51
tcctcgttag tatagtggtg agtatccccg cctgtcaccc gcgagaccgg cgttccattc    60
cccgacgggg agacgtagcc ccacctcgga aacctgatca tgtagatcga atggactcta   120
aatccgttca gccgggttag attcccgggg tttccgtagc gtcctttttg gaaagacaag   180
gtgcgtcgta gtcggcgttg tcctcgttag tatagtggtg agtatccccg cctgtcaccc   240
gcgagaccgg cgttccattc cccgacgggg agacgtagcc ccacctcgga aacctgatca   300
tgtagatcga atggactcta aatccgttca gccgggttag attcccgggg tttccgtagc   360
gtccttttt                                                           369

<210> SEQ ID NO 52
<211> LENGTH: 21
<212> TYPE: DNA
<213> ORGANISM: Artificial sequence
<220> FEATURE:
<223> OTHER INFORMATION: Synthetic sequence: Leader sequence used in the
      2xAsp-pyl construct

<400> SEQUENCE: 52
ggtgcgtcgt agtcggcgtt g                                              21

<210> SEQ ID NO 53
<211> LENGTH: 13
<212> TYPE: DNA
<213> ORGANISM: Artificial sequence
<220> FEATURE:
<223> OTHER INFORMATION: Synthetic sequence: Terminator sequence used in
``` the 2xAsp-pyl construct

<400> SEQUENCE: 53
tagcgtcctt ttt                                                         13

<210> SEQ ID NO 54
<211> LENGTH: 15
<212> TYPE: DNA
<213> ORGANISM: Artificial sequence
<220> FEATURE:
<223> OTHER INFORMATION: Synthetic sequence: intergene sequence used in
      the tRNAasp-pyl constructs

<400> SEQUENCE: 54
acgtagcccc acctc                                                       15

<210> SEQ ID NO 55
<211> LENGTH: 72
<212> TYPE: DNA
<213> ORGANISM: Homo sapiens

<400> SEQUENCE: 55
tccctggtgg tctagtggct aggattcggc gctttcaccg ccgcggcccg ggttcgattc       60
ccggtcagga at                                                          72

<210> SEQ ID NO 56
<211> LENGTH: 70
<212> TYPE: DNA
<213> ORGANISM: Homo sapiens

<400> SEQUENCE: 56
tccttgttag tatagtggtg agtgtttctg cctgtcatgt ggagactgga gtttgagtcc      60
ccaacaggga                                                             70

<210> SEQ ID NO 57
<211> LENGTH: 61
<212> TYPE: DNA
<213> ORGANISM: Artificial sequence
<220> FEATURE:
<223> OTHER INFORMATION: Synthetic sequence: 7SL promoter variant: 7SL-1

<400> SEQUENCE: 57
cgctccccaa tgacgtaact gccctgcagc ttctagtagc ttttcgcagc gtctccgacc       60
g                                                                      61

<210> SEQ ID NO 58
<211> LENGTH: 62
<212> TYPE: DNA
<213> ORGANISM: Artificial sequence
<220> FEATURE:
<223> OTHER INFORMATION: Synthetic sequence: 7SL promoter variant: 7SL-2

<400> SEQUENCE: 58
tctggttgct accatgtgta gcctgcaagc ctctagcagc tcttttgcag cgacgccgac       60
cg                                                                     62

<210> SEQ ID NO 59
<211> LENGTH: 62
<212> TYPE: DNA
<213> ORGANISM: Artificial sequence
<220> FEATURE:
<223> OTHER INFORMATION: Synthetic sequence: 7SL promoter variant: SL28

<400> SEQUENCE: 59
taacattgct aatgagtttt gggcacacat tgtcattgat aacatcttat caggagacag    60
gg    62

<210> SEQ ID NO 60
<211> LENGTH: 49
<212> TYPE: DNA
<213> ORGANISM: Artificial sequence
<220> FEATURE:
<223> OTHER INFORMATION: Synthetic sequence: 7SL promoter variant: 7L63

<400> SEQUENCE: 60
acagaggaac taccataaca agaaccaaag agaaatggca tacctcagg    49

<210> SEQ ID NO 61
<211> LENGTH: 44
<212> TYPE: DNA
<213> ORGANISM: Artificial sequence
<220> FEATURE:
<223> OTHER INFORMATION: Synthetic sequence: 7SL promoter variant: 7L23

<400> SEQUENCE: 61
ctccctctca aaactcaagg aaatctagtg ggcatggtgc acat    44

<210> SEQ ID NO 62
<211> LENGTH: 49
<212> TYPE: DNA
<213> ORGANISM: Artificial sequence
<220> FEATURE:
<223> OTHER INFORMATION: Synthetic sequence: 7SL promoter variant: 7L7

<400> SEQUENCE: 62
aggtactacc caatggtttt ctaaaatact tgcatctgca catgccatg    49

<210> SEQ ID NO 63
<211> LENGTH: 160
<212> TYPE: DNA
<213> ORGANISM: Artificial sequence
<220> FEATURE:
<223> OTHER INFORMATION: Synthetic sequence: EBER promoter variant:
      EBER1

<400> SEQUENCE: 63
gatccaaact tttgttttag gatttatgca tccattatcc cgcagttcca cctaaacggg    60
gcttaacgtt gcatcccaga agatgcacgc ttaaccccgc ctacaaccgt gacgtagctg    120
tttaccagca tgtatagagt tacggttcgc tacatcaaac    160

<210> SEQ ID NO 64
<211> LENGTH: 100
<212> TYPE: DNA
<213> ORGANISM: Artificial sequence
<220> FEATURE:
<223> OTHER INFORMATION: Synthetic sequence: Vault promoter variant:
      Hvg3

<400> SEQUENCE: 64
aggtcgctga gtcaagctaa agcaccgttg ttttgactca ctctttgtga cgtaggtctt    60
tctcaccagt caagaaaata caatccgaaa gcaacctctg    100

<210> SEQ ID NO 65
<211> LENGTH: 98
<212> TYPE: DNA
<213> ORGANISM: Artificial sequence
<220> FEATURE:
<223> OTHER INFORMATION: Synthetic sequence: Vault promoter variant: Hvg3

<400> SEQUENCE: 65
tggttgctga gtcatgctaa aacactgttg ttttgactca ctttgtgacg taggtctttc    60
tcaccagtca agaaaatata atccggagat agcctctg                            98

<210> SEQ ID NO 66
<211> LENGTH: 454
<212> TYPE: PRT
<213> ORGANISM: Methanosarcina mazei

<400> SEQUENCE: 66

```
Met Asp Lys Lys Pro Leu Asn Thr Leu Ile Ser Ala Thr Gly Leu Trp
1               5                   10                  15

Met Ser Arg Thr Gly Thr Ile His Lys Ile Lys His His Glu Val Ser
            20                  25                  30

Arg Ser Lys Ile Tyr Ile Glu Met Ala Cys Gly Asp His Leu Val Val
        35                  40                  45

Asn Asn Ser Arg Ser Ser Arg Thr Ala Arg Ala Leu Arg His His Lys
    50                  55                  60

Tyr Arg Lys Thr Cys Lys Arg Cys Arg Val Ser Asp Glu Asp Leu Asn
65                  70                  75                  80

Lys Phe Leu Thr Lys Ala Asn Glu Asp Gln Thr Ser Val Lys Val Lys
                85                  90                  95

Val Val Ser Ala Pro Thr Arg Thr Lys Lys Ala Met Pro Lys Ser Val
            100                 105                 110

Ala Arg Ala Pro Lys Pro Leu Glu Asn Thr Glu Ala Ala Gln Ala Gln
        115                 120                 125

Pro Ser Gly Ser Lys Phe Ser Pro Ala Ile Pro Val Ser Thr Gln Glu
    130                 135                 140

Ser Val Ser Val Pro Ala Ser Val Ser Thr Ser Ile Ser Ile Ser
145                 150                 155                 160

Thr Gly Ala Thr Ala Ser Ala Leu Val Lys Gly Asn Thr Asn Pro Ile
                165                 170                 175

Thr Ser Met Ser Ala Pro Val Gln Ala Ser Ala Pro Ala Leu Thr Lys
            180                 185                 190

Ser Gln Thr Asp Arg Leu Glu Val Leu Leu Asn Pro Lys Asp Glu Ile
        195                 200                 205

Ser Leu Asn Ser Gly Lys Pro Phe Arg Glu Leu Glu Ser Glu Leu Leu
    210                 215                 220

Ser Arg Arg Lys Lys Asp Leu Gln Gln Ile Tyr Ala Glu Glu Arg Glu
225                 230                 235                 240

Asn Tyr Leu Gly Lys Leu Glu Arg Glu Ile Thr Arg Phe Phe Val Asp
                245                 250                 255

Arg Gly Phe Leu Glu Ile Lys Ser Pro Ile Leu Ile Pro Leu Glu Tyr
            260                 265                 270

Ile Glu Arg Met Gly Ile Asp Asn Asp Thr Glu Leu Ser Lys Gln Ile
        275                 280                 285

Phe Arg Val Asp Lys Asn Phe Cys Leu Arg Pro Met Leu Ala Pro Asn
    290                 295                 300

Leu Tyr Asn Tyr Leu Arg Lys Leu Asp Arg Ala Leu Pro Asp Pro Ile
305                 310                 315                 320

Lys Ile Phe Glu Ile Gly Pro Cys Tyr Arg Lys Glu Ser Asp Gly Lys
```

|  | 325 |  |  |  |  | 330 |  |  |  |  | 335 |  |  |
|---|---|---|---|---|---|---|---|---|---|---|---|---|---|

Glu His Leu Glu Glu Phe Thr Met Leu Asn Phe Cys Gln Met Gly Ser
    340                    345                  350

Gly Cys Thr Arg Glu Asn Leu Glu Ser Ile Ile Thr Asp Phe Leu Asn
    355                    360                  365

His Leu Gly Ile Asp Phe Lys Ile Val Gly Asp Ser Cys Met Val Tyr
    370                    375                  380

Gly Asp Thr Leu Asp Val Met His Gly Asp Leu Glu Leu Ser Ser Ala
385                    390                  395                  400

Val Val Gly Pro Ile Pro Leu Asp Arg Glu Trp Gly Ile Asp Lys Pro
            405                  410                  415

Trp Ile Gly Ala Gly Phe Gly Leu Glu Arg Leu Leu Lys Val Lys His
            420                  425                  430

Asp Phe Lys Asn Ile Lys Arg Ala Ala Arg Ser Glu Ser Tyr Tyr Asn
            435                  440                  445

Gly Ile Ser Thr Asn Leu
    450

<210> SEQ ID NO 67
<211> LENGTH: 1365
<212> TYPE: DNA
<213> ORGANISM: Methanosarcina mazei

<400> SEQUENCE: 67

```
atggataaaa aaccattgaa tacgctcatt agcgcaactg gctgtggat gagccgtacg      60
ggaacgattc ataaaatcaa gcaccacgaa gtatctcgta gcaaaatcta tatcgagatg     120
gcttgcggcg accatctcgt ggtaaacaat agcaggtcct cacggaccgc ccgtgccttg     180
cgccaccaca aatatcgtaa aacttgtaag agatgtagag tgagcgacga ggatctgaac     240
aagtttctta caaaggccaa cgaggaccaa accagcgtca agtcaaggt tgtgagcgcc     300
ccaacacgca ccaagaaggc catgcccaag tctgttgcgc gggcaccgaa acctctggag     360
aatactgagg ccgctcaggc ccagcccagc ggttcaaaat tctctcctgc cattccagtt     420
agcactcaag agtcagtcag cgtgcccgcc tctgtgtcta catccatcag ctctatctcc     480
accggcgcaa cagcctctgc cctggtgaag ggtaatacga accctatcac gagtatgtcc     540
gcacccgtgc aagcaagtgc tcccgcactc actaaatccc aaacggaccg gctgaggtc      600
ctgcttaacc ctaaggatga atcagcctg aacagtggaa aaccgtttcg agaactggaa       660
tccgagctct taagccggcg aaagaaagat ttgcaacaga tttacgccga gaacgggaa       720
aattatctgg gcaagctgga gagagaaatc actaggttct ttgtagatag ggctttctg       780
gagattaaga gtcccatatt gatccctctc gaatacattg agcgtatggg catcgacaac     840
gacacagaac ttagcaagca gatctttcgg gtggacaaaa acttctgcct caggcctatg     900
ctggctccaa atctgtacaa ctatcttagg aaactcgacc gggccctgcc cgatcccatt     960
aaaatcttcg aaattggacc ttgctataga aggagagcg atggcaagga gcacctggag    1020
gagtttacta tgctcaattt ctgtcaaatg ggctccggct gcacacgtga gaacctcgaa    1080
tccattataa ccgacttcct gaatcacctg gggattgatt tcaagatcgt gggcgactcc    1140
tgcatggtgt ttggtgatac gttggatgtg atgcacggag atttggaatt gtcaagcgct    1200
gtggtaggcc ccattcctct cgacagggag tggggtattg acaagccctg gatcggcgca    1260
ggttttggac tggagcgcct gttgaaggtt aagcatgact tcaaaaacat aaagagagcc    1320
gcacgcagcg aatcctatta taatggaatc agcactaact tgtaa                    1365
```

<210> SEQ ID NO 68
<211> LENGTH: 10
<212> TYPE: DNA
<213> ORGANISM: Artificial sequence
<220> FEATURE:
<223> OTHER INFORMATION: Synthetic sequence: Spacer region

<400> SEQUENCE: 68
ctttgtttct                                                            10

<210> SEQ ID NO 69
<211> LENGTH: 105
<212> TYPE: DNA
<213> ORGANISM: Artificial sequence
<220> FEATURE:
<223> OTHER INFORMATION: Synthetic construct

<400> SEQUENCE: 69
atggtcgctg agtcatgctg aagcactctc tttttgactc actctttgtg acgtaggtct     60
ttctcaccag tcaataaaat ataatccgaa agcaacctcc cacca                    105

<210> SEQ ID NO 70
<211> LENGTH: 80
<212> TYPE: DNA
<213> ORGANISM: Artificial sequence
<220> FEATURE:
<223> OTHER INFORMATION: Synthetic construct

<400> SEQUENCE: 70
gcacgcttaa ccccgcctac aaccgtgacg tagctgttta ccagcatgta tagagttacg     60
gttcgctaca tcaaacacca                                                 80

<210> SEQ ID NO 71
<211> LENGTH: 75
<212> TYPE: DNA
<213> ORGANISM: Artificial sequence
<220> FEATURE:
<223> OTHER INFORMATION: Synthetic construct

<400> SEQUENCE: 71
ccagtagata tcccagttga tgacgtcacc ataccacagc ttctagtgct attctgcgcc     60
ggtatccgac cacca                                                      75

<210> SEQ ID NO 72
<211> LENGTH: 69
<212> TYPE: DNA
<213> ORGANISM: Methanosarcina barkeri

<400> SEQUENCE: 72
gggaacctga tcatgtagat cgaatggact ctaaatccgt tcagccgggt tagattcccg     60
gggtttccg                                                             69

<210> SEQ ID NO 73
<211> LENGTH: 69
<212> TYPE: DNA
<213> ORGANISM: Artificial sequence
<220> FEATURE:
<223> OTHER INFORMATION: Synthetic sequence: Mb pyltRNA (A+B box)

<400> SEQUENCE: 73
gggaacctgc tcaggtagag cgaatggact ctaaatccgt tcagccgggt tcgattcccg     60

```
gggtttccg                                                            69

<210> SEQ ID NO 74
<211> LENGTH: 69
<212> TYPE: DNA
<213> ORGANISM: Artificial sequence
<220> FEATURE:
<223> OTHER INFORMATION: Synthetic sequence: Mm pyltRNA (A+B box)

<400> SEQUENCE: 74
ggaaacctgg tcaagtagat cgaatggact ctaaatccgt tcagccgggt tcgattcccg    60
gggtttccg                                                            69

<210> SEQ ID NO 75
<211> LENGTH: 25
<212> TYPE: DNA
<213> ORGANISM: Homo sapiens

<400> SEQUENCE: 75
tgacgtaggt ctttctcacc agtca                                          25

<210> SEQ ID NO 76
<211> LENGTH: 21
<212> TYPE: DNA
<213> ORGANISM: Epstein-Barr virus

<400> SEQUENCE: 76
gcacgcttaa ccccgcctac a                                              21

<210> SEQ ID NO 77
<211> LENGTH: 19
<212> TYPE: DNA
<213> ORGANISM: Epstein-Barr virus

<400> SEQUENCE: 77
accgtgacgt agctgttta                                                 19

<210> SEQ ID NO 78
<211> LENGTH: 9
<212> TYPE: DNA
<213> ORGANISM: Homo sapiens

<400> SEQUENCE: 78 tgacgtcac                                                             9

<210> SEQ ID NO 79
<211> LENGTH: 10
<212> TYPE: DNA
<213> ORGANISM: Homo sapiens

<400> SEQUENCE: 79
ttctagtgct                                                           10

<210> SEQ ID NO 80
<211> LENGTH: 11
<212> TYPE: DNA
<213> ORGANISM: Artificial sequence
<220> FEATURE:
<223> OTHER INFORMATION: Synthetic sequence: Spacer region

<400> SEQUENCE: 80
ccccaaacct c                                                         11
```

```
<210> SEQ ID NO 81
<211> LENGTH: 12
<212> TYPE: DNA
<213> ORGANISM: Artificial sequence
<220> FEATURE:
<223> OTHER INFORMATION: Synthetic sequence: Spacer region

<400> SEQUENCE: 81
tagccccacc tc                                                              12
```